(12) United States Patent
Nobile et al.

(10) Patent No.: US 8,673,627 B2
(45) Date of Patent: Mar. 18, 2014

(54) APPARATUS AND METHODS FOR PERFORMING ELECTROCHEMICAL REACTIONS

(75) Inventors: John Nobile, Guilford, CT (US); Thomas Roth, Guilford, CT (US); Todd Rearick, Cheshire, CT (US); Jonathan Schultz, Oxford, MA (US); Jonathan Rothberg, Guilford, CT (US); David Marran, Durham, CT (US)

(73) Assignee: Life Technologies Corporation, Carlsbad, CA (US)

( * ) Notice: Subject to any disclaimer, the term of this patent is extended or adjusted under 35 U.S.C. 154(b) by 478 days.

(21) Appl. No.: 12/785,716

(22) Filed: May 24, 2010

(65) Prior Publication Data

US 2010/0300895 A1 Dec. 2, 2010

Related U.S. Application Data

(63) Continuation-in-part of application No. 12/474,897, filed on May 29, 2009, and a continuation-in-part of application No. 12/475,311, filed on May 29, 2009, now abandoned.

(60) Provisional application No. 61/306,924, filed on Feb. 22, 2010.

(51) Int. Cl.
*C12M 1/34* (2006.01)
*C12M 3/00* (2006.01)
*C12M 1/00* (2006.01)
*C12Q 1/68* (2006.01)
*G01N 27/403* (2006.01)

(52) U.S. Cl.
USPC ....... 435/287.2; 435/6.1; 435/283.1; 257/253

(58) Field of Classification Search
USPC .................. 435/6, 6.1, 283.1, 287.1, 287.2; 257/253
See application file for complete search history.

(56) References Cited

U.S. PATENT DOCUMENTS

| | | | |
|---|---|---|---|
| 4,411,741 A | 10/1983 | Janata | |
| 4,438,354 A | 3/1984 | Haque et al. | |

(Continued)

FOREIGN PATENT DOCUMENTS

| | | |
|---|---|---|
| CN | 102203282 | 9/2011 |
| EP | 0223618 | 5/1987 |

(Continued)

OTHER PUBLICATIONS

[No Author Listed], "ISFET Wikipedia article", *Wikipedia*, Last modified Nov. 7, 2006.

(Continued)

*Primary Examiner* — Robert T. Crow

(57) ABSTRACT

The invention is directed to apparatus and methods for delivering multiple reagents to, and monitoring, a plurality of analytical reactions carried out on a large-scale array of electronic sensors under minimal noise conditions. In one aspect, the invention provides method of improving signal-to-noise ratios of output signals from the electronic sensors sensing analytes or reaction byproducts by subtracting an average of output signals measured from neighboring sensors where analyte or reaction byproducts are absent. In other aspects, the invention provides an array of electronic sensors integrated with a microwell array for confining analytes and/or particles for analytical reactions and a method for identifying microwells containing analytes and/or particles by passing a sensor-active reagent over the array and correlating sensor response times to the presence or absence of analytes or particles. Such detection of analyte- or particle-containing microwells may be used as a step in additional noise reduction methods.

14 Claims, 21 Drawing Sheets

(56) References Cited

U.S. PATENT DOCUMENTS

| | | |
|---|---|---|
| 4,490,678 A | 12/1984 | Kuisl et al. |
| 4,743,954 A | 5/1988 | Brown |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,971,903 A | 11/1990 | Hyman |
| 5,038,192 A | 8/1991 | Bonneau et al. |
| 5,110,441 A | 5/1992 | Kinlen et al. |
| 5,138,251 A * | 8/1992 | Koshiishi et al. ............ 324/71.5 |
| 5,142,236 A | 8/1992 | Maloberti et al. |
| 5,151,759 A | 9/1992 | Vinal |
| 5,164,319 A | 11/1992 | Hafeman et al. |
| 5,317,407 A | 5/1994 | Michon |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,554,339 A | 9/1996 | Cozzette et al. |
| 5,593,838 A | 1/1997 | Zanzucchi et al. |
| 5,600,451 A | 2/1997 | Maki |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,911,873 A | 6/1999 | McCarron et al. |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,107,032 A | 8/2000 | Kilger et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,511,803 B1 | 1/2003 | Church et al. |
| 6,518,024 B2 | 2/2003 | Choong et al. |
| 6,518,146 B1 | 2/2003 | Singh et al. |
| 6,537,881 B1 | 3/2003 | Rangarajan et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,700,814 B1 | 3/2004 | Nahas et al. |
| 6,780,591 B2 | 8/2004 | Williams et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,919,211 B1 | 7/2005 | Fodor et al. |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi et al. |
| 7,192,745 B2 | 3/2007 | Jaeger |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,394,263 B2 | 7/2008 | Pechstein et al. |
| 7,455,971 B2 | 11/2008 | Chee et al. |
| 7,462,512 B2 | 12/2008 | Levon et al. |
| 7,465,512 B2 | 12/2008 | Wright et al. |
| 7,470,352 B2 | 12/2008 | Eversmann et al. |
| 7,575,865 B2 | 8/2009 | Leamon et al. |
| 7,595,883 B1 | 9/2009 | El Gamal et al. |
| 7,608,810 B2 | 10/2009 | Yamada |
| 7,667,501 B2 | 2/2010 | Surendranath et al. |
| 7,785,790 B1 | 8/2010 | Church et al. |
| 7,859,029 B2 | 12/2010 | Lee et al. |
| 7,888,013 B2 | 2/2011 | Miyahara et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0044799 A1 * | 3/2003 | Matson ........................ 435/6 |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0108867 A1 | 6/2003 | Chee et al. |
| 2003/0124599 A1 | 7/2003 | Chen et al. |
| 2003/0138809 A1 | 7/2003 | Williams et al. |
| 2003/0148301 A1 | 8/2003 | Aono et al. |
| 2003/0148344 A1 | 8/2003 | Rothberg et al. |
| 2003/0157504 A1 | 8/2003 | Chee et al. |
| 2003/0186262 A1 | 10/2003 | Cailloux |
| 2003/0194740 A1 | 10/2003 | Williams |
| 2003/0215857 A1 | 11/2003 | Kilger et al. |
| 2003/0224419 A1 | 12/2003 | Corcoran et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |

(56) References Cited

U.S. PATENT DOCUMENTS

| | | |
|---|---|---|
| 2004/0049237 A1 | 3/2004 | Larson et al. |
| 2004/0130377 A1 | 7/2004 | Takeda et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0019842 A1* | 1/2005 | Prober et al. ............. 435/7.9 |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1* | 3/2005 | Guia et al. ............. 435/5 |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1* | 6/2005 | Glezer et al. ............. 422/58 |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1* | 12/2005 | Fouillet et al. ............. 435/6 |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057604 A1 | 3/2006 | Chen et al. |
| 2006/0073513 A1 | 4/2006 | Chee et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke |
| 2006/0182664 A1 | 8/2006 | Peck et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0205061 A1 | 9/2006 | Roukes |
| 2006/0216812 A1* | 9/2006 | Okada et al. ............. 435/286.5 |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117137 A1 | 5/2007 | Jaeger |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1* | 2/2008 | Toumazou et al. ............. 435/6 |
| 2008/0035494 A1 | 2/2008 | Gomez et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286762 A1 | 11/2008 | Miyahara et al. |
| 2008/0286767 A1 | 11/2008 | Miyahara et al. |
| 2009/0026082 A1 | 1/2009 | Rothberg et al. |
| 2009/0030117 A1 | 1/2009 | Lanphere et al. |
| 2009/0032401 A1 | 2/2009 | Ronaghi et al. |
| 2009/0048124 A1 | 2/2009 | Leamon et al. |
| 2009/0079414 A1 | 3/2009 | Levon et al. |
| 2009/0108831 A1 | 4/2009 | Levon et al. |
| 2009/0127589 A1 | 5/2009 | Rothberg et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0273386 A1 | 11/2009 | Korobeynikow et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0165557 A1 | 7/2011 | Ah et al. |
| 2011/0217697 A1 | 9/2011 | Rothberg et al. |
| 2011/0263463 A1 | 10/2011 | Rothberg et al. |
| 2011/0275522 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife |
| 2012/0001237 A1 | 1/2012 | Fife et al. |
| 2012/0001615 A1 | 1/2012 | Levine |
| 2012/0001646 A1 | 1/2012 | Bolander et al. |
| 2012/0001685 A1 | 1/2012 | Levine et al. |
| 2012/0022795 A1 | 1/2012 | Johnson et al. |
| 2012/0040844 A1 | 2/2012 | Rothberg et al. |
| 2012/0056248 A1 | 3/2012 | Fife |
| 2012/0129728 A1 | 5/2012 | Rothberg et al. |
| 2012/0129732 A1 | 5/2012 | Rothberg et al. |

FOREIGN PATENT DOCUMENTS

| | | |
|---|---|---|
| EP | 1371974 | 12/2003 |
| EP | 1432818 | 6/2004 |
| EP | 1542009 | 6/2005 |
| EP | 2307577 | 4/2011 |
| GB | 2457851 | 9/2009 |
| GB | 2461127 B | 7/2010 |
| JP | 2002272463 | 9/2002 |
| JP | 2005-518541 | 6/2005 |
| JP | 2011-525810 | 9/2011 |
| KR | 10-0442838 | 7/2004 |
| KR | 10-0455283 | 10/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/42498 | 6/2001 |
| WO | WO-01/81896 | 11/2001 |

(56) References Cited

FOREIGN PATENT DOCUMENTS

| WO | WO-02/077287 | 10/2002 |
|---|---|---|
| WO | WO-02/086162 | 10/2002 |
| WO | WO-03/073088 | 9/2003 |
| WO | WO-2004/040291 | 5/2004 |
| WO | WO-2005/047878 | 5/2005 |
| WO | WO-2005/084367 | 9/2005 |
| WO | WO-2006/022370 | 3/2006 |
| WO | WO-2007/086935 | 8/2007 |
| WO | WO-2008/007716 | 1/2008 |
| WO | WO-2008/058282 | 5/2008 |
| WO | WO-2008/076406 | 6/2008 |
| WO | WO-2008/107014 | 9/2008 |
| WO | WO-2009/012112 | 1/2009 |
| WO | 2009/158006 | 12/2009 |
| WO | WO-2009/158006 | 12/2009 |
| WO | WO-2010/008480 | 1/2010 |
| WO | WO-2010/047804 | 4/2010 |
| WO | WO-2010/047804 A8 | 4/2010 |
| WO | WO-2010/138182 | 12/2010 |
| WO | WO-2010/138188 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |

OTHER PUBLICATIONS

Ahmadian, A. et al., "Single-nucleotide polymorphism analysis by pyrosequencing", *Anal. Biochem*, vol. 280, 2000, pp. 103-110.

Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.

AU2011226767 Search Information Statement Mailed Oct. 26, 2011, pp. 1-3.

Bandiera, L et al., "A fully electronic sensor for the measurement of cDNA hybridization kinetics", *Biosens Bioelectron*, vol. 22, 2007, pp. 2108-2114.

Barbaro, M et al., "A Charge-Modulated FET for Detection of Biomolecular Processes: Conception, Modeling, and Simulation", *IEEE Transactions on Electron Devices*, vol. 53(1), 2006, pp. 158-166.

Barbaro, M et al., "A CMOS, Fully Integrated Sensor for Electronic Detection of DNA Hybridization", *IEEE Electron Device Letters*, vol. 27(7), 2006, pp. 595-597.

Barbaro, M et al., "Fully electronic DNA hybridization detection by a standard CMOS biochip", *Sensors and Actuators B Chemical*, vol. 118, 2006, pp. 41-46.

Bashford, G et al., "Automated bead-trapping apparatus and control system for single-molecule DNA sequencing", *Optics Express*, vol. 16(5), Mar. 3, 2008, pp. 3445-3455.

Baumann, W et al., "Microelectronic sensor system for microphysiological application on living cells", *Sensors Actuators B*, vol. 55, 1999, pp. 77-89.

Bausells, J et al., "Ion-sensitive field-effect transistors fabricated in a commercial CMOS technology", *Sensors and Actuators B Chemical*, vol. 57, 1999, pp. 56-62.

Bergveld, P., "ISFET, Theory and Practice", *IEEE Sensor Conference*, Toronto, Oct. 2003, 2003, pp. 1-26.

Bergveld, P., "Thirty years of ISFETOLOGY What happened in the past 30 years and what may happen in the next 30 years", *Sensors and Actuators B*, vol. 88, vol. 88, 2003, pp. 1-20.

Besselink, G et al., "ISFET Affinity Sensor", *Methods in Biotechnology*, vol. 7: Affinity Biosensors: Techniques and Protocols, 1998, pp. 173-185.

Bobrov, p. et al., "Chemical sensitivity of an ISFET with Ta2O5 membrane in strong acid and alkaline solutions", *Sensors and Actuators B*, vol. 3, 1991, pp. 75-81.

Bousse, L et al., "A process for the combined fabrication of ion sensors and CMOS circuits", *IEEE Electron Device Letters*, vol. 9(1), 1988, pp. 44-46.

Bousse, L et al., "Zeta potential measurements of Ta2O5 and SiO2 thin films", *J. Colloid Interface Sci.*, vol. 147(1), 1991, pp. 22-32.

Chen, et al., "Nanoscale field effect transistor for biomolecular signal amplification", *App Phys Letter*, vol. 91, 2007, pp. 243511-1-243511-3.

Chen, et al., "Silicon-based nanoelectronic field-effect pH sensor with local gate control", *App Phys Letter*, vol. 89, 2006, pp. 223512-1-223512-3.

Chou, J. et al., "Letter to the Editor on Simulation of Ta2O5 gate ISFET temperature characteristics", *Sensors and Actuators B*, vol. 80, 2001, pp. 290-291.

Chou, J. et al., "Simulation of Ta2O5 gate ISFET temperature characteristics", *Sensor and Actuators B*, vol. 71, Letter to the Editor, 2000, pp. 73-61.

Chung, W-Y et al., "ISFET interface circuit embedded with noise rejection capability", *Electronics Letters*, vol. 40(18), e-pub ; 2 pages, 2004.

Chung, W-Y et al., "ISFET performance enhancement by using the improved circuit techniques", *Sensors and Actuators B*, vol. 113, 2006, pp. 555-562.

Eijkel, J. et al., "Measuring Donnan-related phenomena using a solid-state ion sensor and a concentration-step method", *J. Membrane Sci.*, vol. 127, 1997, pp. 203-221.

Eijkel, J., "Potentiometric detection and characterization of adsorbed protein using stimulus-response measurement techniques", *Thesis*, Sep. 3, 1955, pp. 1-147; 160-192.

Eltoukhy, H et al., "A 0.18um CMOS 10-6 lux Bioluminescence Detection System-on-Chip", *ISSCC 2004/Session12/Biomicrosystems/12.3*, 2004, pp. 1-3.

Eltoukhy, H. et al., "A. 0.18-um CMOS Bioluminescence Detection Lab-on-Chip", *IEEE J Solid-State Circuits*, vol. 41(3), 2006, pp. 651-662.

EP7867780.4 Examination Report Mailed Jul. 3, 2012.

Eriksson, J et al., "Pyrosequencing technology at elevated temperature", *Electrophoresis*, vol. 25. 2004, pp. 20-27.

Esfandyarpour, H. et al. "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.

Eversmann, B. et al., "A 128×128 CMOS Biosensor Array for Extracellular Recording of Neural Activity", *IEEE J. Solid-State Circ.*, vol. 38(12), Dec. 12, 2003, pp. 2306-2317.

Faramarzpour, N. et al., "CMOS-Based Active Pixel for Low-Light Level Detection: Analysis and Measurements", *IEEE Trans Electron Devices*, vol. 54(12), 2007, pp. 3229-3237.

Finn, A et al., "Towards an Optimization of FET-Based Bio-Sensors", *European Cells and Materials*, vol. 4, Sup 2, 2002, pp. 21-23.

Fraden, J., "Handbook of Modern Sensors—Physics, Designs, and Applications . . .", *17.3.2 CHEMFET Sensors*, 1996, pp. 499-501.

Fritz, et al., "Electronic detection of DNA by its intrinsic molecular charge", *PNAS*, vol. 99(22),2002, pp. 14142-14146.

GB0811656.8 Search and Examination Report Mailed Mar. 12, 2010.

GB0811656.8 Search Report Mailed Sep. 21, 2009.

GB0811657.6 Examination Report Mailed Jun. 30, 2010.

GB0811657.6 Search Report under Section 17 Mailed Oct. 26, 2009.

Gracia, I. et al., "Test Structures for ISFET Chemical Sensors", *Proc IEEE 1992 Intl Conf Microelec Test Struct*, vol. 5, 1992, pp. 156-159.

Hammond, P. et al., "A System-on-Chip Digital pH Meter for Use in a Wireless Diagnostic Capsule", *IEEE Transactons on Biomedical Engineering*, vol. 52(4), 2005, pp. 687-694.

Hammond, P. et al., "Design of a Single-Chip pH Sensor Using a Conventional 0.6-μm CMOS Process", *IEEE Sensors Journal*, vol. 4(6), 2004, pp. 706-712.

Hammond, P. et al., "Encapsulation of a liquid-sensing microchip using SU-8 photoresist", *MicoElectronic Engineering*, vol. 73-74, 2004, pp. 893-897.

Hammond, S. et al., "Genomic sequencing and analysis of a Chinese Hampster ovary cell line using Illumina sequencing technology", *BMC Genomics*, 12:67, 2011, pp. 1-8.

Han, Y., "Label-free detection of biomolecules by a field-effect transistor microarray biosensor with bio-functionalized gate surfaces", Masters Dissertation, 2006, pp. 1-63.

(56) References Cited

OTHER PUBLICATIONS

Hara, H. et al., "Dynamic response of a Ta2O5-gate pH-sensitive field-effect transistor", *Sensors Actuators B*, vol. 32, 1996, pp. 115-119.
Hermon, Z. et al. "Miniaturized bio-electronic hybrid for chemical sensing applications", *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, 117, 2006, pp. 509-515.
Hizawa, T. et al., "32×32 pH Image Sensors for Real Time Observation of Biochemical Phenomena", *Transducers & Eurosensors '07*, 14th International Conference on Solid-State, Actuators and Microsystems, Lyon, France, Jun. 10-14, 2007, 2007, pp. 1311-1312.
Jakobson, C. et al., "Low frequency noise and drift in Ion Senstive Field Effect Transistors", *Sensors Actuators B*, vol. 68, 2000, pp. 134-139.
Ji, H. et al., "A CMOS contract imager for locating individual cells", *ISCAS*, 2006, pp. 3357-3360.
Ji, H. et al., "Contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), Jul. 30, 2004, pp. 69-74.
Klein, M., "Time effects of ion-sensitive field-effect transistor", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J et al., "A Massively Parallel PicoTiterPlate Based Platform for Discrete Picoliter-Scale Polymerase Chain Reactions", *Electrophoresis*, vol. 24, Nov. 24, 2003, pp. 3769-3777.
Leamon, J. et al., "Cramming More Sequencing Reactions onto Microreactor Chips", *Chemical Reviews*, 107:, 2007, 3367-3376.
Lee, C-S et al., "Ion-sensitive Field-Effect Transistor for Biological Sensing", *Sensors*, vol. 9, 2009, pp. 7111-7131.
Li, et al., "Sequence-Specific Label-Free DNA Sensors Based on Silico Nanowires", *Nano Letters,*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proc. of the 1996 IEEE International Conference on Microelectronic Test Structures*, vol. 9, 1996, pp. 123-128.
Margulies, M. et al., "Genome sequencing in microfabricated high-density picolitre reactors", *Nature*, vol. 437, 2005, pp. 376-380.
Marshall, A. et al., "DNA chips: an array of possibilities", *Nature Biotechnology*, vol. 16, Jan. 1998, pp. 27-31.
Martinoia, S. et al., "A behavioral macromodel of the ISFET in SPICE", *Sensors Actuators B*, vol. 62, 2000, pp. 182-189.
Martinoia, S., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), Jan. 15, 2006, pp. 1037-1044.

Milgrew, M et al., "A large transistor based sensor array chip for direct extracellular imaging", *Sensors and Actuators B Chemical*, vol. 111-112, 2005, pp. 347-353.
Milgrew, M et al., "Microsensor Array Technology for Direct Extracellular Imaging", Apr. 5, 2006, pp. 1-23.
Milgrew, M et al., "The development of scalable sensor arrays using standard CMOS technology", *Sensors and Actuators B*, 103, 2004, pp. 37-42.
Milgrew, M et al., "The fabrication of scalable multi-sensor arrays using standard CMOS technology", *2003 IEEE Custom Integrated Circuits Conference*, 2003, pp. 513-516.
Milgrew, M. et al., "A 16×16 CMOS proton camera array for direct extracellular imaging of hydrogen-ion activity", *IEEE Intl Solid-State Circuits Conf,* Ses. 32:24, 2008, pp. 590-591; 638.
Milgrew, M. et al., "Matching the transconductance characteristics of CMOS ESFET arrays by removing trapped charge", *IEEE Trans Electron Devices*, vol. 55(4), 2008, pp. 1074-1079.
Miyahara, Y et al., "Direct Transduction of Primer Extension into Electrical Signal Using Genetic Field Effect Transistor", *Micro Total Analysis Systems 2004, vol. 1*, 2004, pp. 303-305.
Miyahara, Y. et al., "Biochip Using Micromachining Technology", *J. Institute of Electrostatics, Japan*, vol. 27(6), 2003, pp. 268-272.
Miyahara, Y. et al., "Potentiometric Detection of DNA Molecules Using Field Effect Transistor", *The Japan Society of Applied Physics*, No. 3, 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), Jul. 1, 2006, pp. 4261-4269.
PCT/JP2005/001987 International Search Report Mailed Apr. 5, 2005.
PCT/JP2005/015522 International Search Report Mailed Sep. 27, 2005.
PCT/US/2009/05745 International Preliminary Report on Patentability Issued Apr. 26, 2011.
PCT/US/2009/05745 International Search Report Mailed Dec. 11, 2009.
PCT/US/2009/05745 Written Opinion Mailed Dec. 11, 2009.
PCT/US2007/025721 Declaration of Non-Establishment of International Search Report Mailed Jul. 15, 2008.
PCT/US2007/025721 International Prelimary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011, pp. 1-8.
PCT/US2010/001543 International Search Report and Written Opinion Mailed Oct. 13, 2010, pp. 1-12.
PCT/US2010/001553 International Preliminary Report on Patentability Mailed Dec. 8, 2011, pp. 1-10.
PCT/US2010/001553 International Search Report Mailed Jul. 28, 2010, pp. 1-2.
PCT/US2010/001553 Written Opinion Mailed Jul. 14, 2010, pp. 1-6.

(56) References Cited

OTHER PUBLICATIONS

PCT/US2010/48835 International Search Report and Written Opinion Mailed Dec. 16, 2010, pp. 1-12.
PCT/US2011/042655 International Search Report Mailed Oct. 21, 2011, pp. 1-2.
PCT/US2011/042660 International Search Report Mailed Nov. 2, 2011.
PCT/US2011/042669 International Search Report Mailed Jan. 9, 2012, pp. 1-5.
PCT/US2011/042669 Written Opinion Jan. 9, 2012, pp. 1-5.
PCT/US2011/042683 International Search Report Mailed Feb. 16, 2012.
PCT/US2011/042683 Written Opinon Mailed Feb. 16, 2012.
Poghossian, A. et al., "Functional testing and characterization of ISFETs on wafer level by means of a micro-droplet cell", *Sensors*, vol. 6, 2006, pp. 397-404.
Pourmand, N. et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Ultra-low power precision ISFET readout using global current feedback", *Electronic Lett*, vol. 42(22), Oct. 26, 2006, 2 pages.
Purushothaman, S. et al., "Protons and single nucleotide polymorphism detection: A simple use for the Ion Sensitive Field Effect Transistor", *Sensors and Actuators B Chemical*, vol. 114, No. 2, 2006, pp. 964-968.
Purushothaman, S. et al., "Towards Fast Solid State DNA Sequencing", *IEEE ISCAS 2002 Proceedings*, Circuits and Systems, vol. 4, 2002, pp. IV-169-IV-172.
Rodriguez-Villegas, E., "Solution to trapped charge in FGMOS transistors, vol. 39(19)", *Electronics Letters*, 2003.
Ronaghi, M. et al., "A Sequencing Method Based on Real-Time Pyrophosphate", *Science*, vol. 281, Jul. 17, 1998, pp. 363-365.
Sakata, T. et al., "Cell-based field effect devices fo cell adhesion analysis", *International Conference on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proc. of 2006 Intl. Conf. on Microtechnologies in Medicine and Biology*, May 9-12, 2005, Okinawa, Japan, 2006, pp. 97-100.
Sakata, T. et al., "Direct detection of single nucleotide polymorphism using genetic field effect transistor", *Digest of Papers Microprocesses and Nanotechnology 2004*, Osaka, Japan, Intl. Microprocesses and Nanotechnology Conf., 2004, pp. 226-227.
Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, 2005, pp. 219-222.
Sakata, T. et al., "Direct transduction of allele-specific primer extension into electrical signal using genetic field effect transistor", *Biosensors and Bioelectronics*, vol. 22, 2007, pp. 1311-1316.
Sakata, T. et al., "DNA Analysis Chip Based on Field-Effect Transistors", *Japanese Journal of Applied Physics*, vol. 44, No. 4B, 2005, pp. 2854-2859.
Sakata, T. et al., "DNA Sequencing Based on Intrinsic Molecular Charges", *Angewandte Chemie International Edition*, 2006, vol. 45, 2006, pp. 2225-2228.

Sakata, T. et al., "DNA Sequencing Based on Intrinsic Molecular Charges", *Angewandte Chemie International Edition*, 2006, vol. 118, 2006, pp. 2283-2286.
Sakata, T. et al., "DNA Sequencing Using Genetic Field Effect Transistor", *13th International Conference on Solid-State Sensors, Actuators and Microsystems*, Jun. 5-9, 2005, Seoul, Korea, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44, No. 4B, 2005, 2005, pp. 2860-2863.
Sakata, T. et al., "Potential Response of Genetic Field Transistor to Charaged Nanoparticle-DNA Conjugate", *Digest of Papers Microprocesses and Nanotechnology 2005*, Tokyo, Japan, 2005 Intl Microprocesses and Nanotech Conf., Hotel Bellclassic, 2005, pp. 42-43.
Sakata, T. et al., "Potentiometric Detection of Allele Specific Oligonucleotide Hybridization Using Genetic Field Effect Transistor", *Micro Total Anslysis Systems 2004*, vol. 1, 8th International Conference on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proc.*, vol. 782, Micro- and Nanosystems, Dec. 1-3, 2003, Boston, Massachusetts, 2004, pp. 393-398.
Sakata, T. et al., "Potentiometric Detection of DNA Using Genetic Transistor", *Denki Gakkai Kenkyukai Shiryo Chemical Sensor Kenkyukai*, CHS-03-51-55, 2003, pp. 1-5.
Sakata, T. et al., "Potentiometric Detection of Single Nucleotide Polymorphism by Using a Genetic Field-effect transistor", *ChemBioChem 2005*, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", *Thesis*, Presented at Stanford University, 2005, pp. ii-78.
Salama, K., "Modeling and simulation of luminescence detection platforms", *Biosensors & Bioelectronics*, 2004, 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, B. et al., "A new approach to immunoFET operation", *Biosensors & Bioelectronics*, vol. 5, 1990, pp. 103-124.
Schasfoort, RB et al., "Field-effect flow control for microfabricated fluidic networks", *Science*, vol. 286(5441), Oct. 29, 1999, pp. 942-945.
Schoning, M. et al., "Bio FEDs (Field-Effect Devices): State-of-the-Art and New Directions", *Electroanalysis*, vol. 18(19-20), 2006, pp. 1893-1900.
SG200903992-6 Search and Examination Report (Favourable) Mailed Jan. 20, 2011.
Shah, N., "Microfabrication of a parellel-array DNA pyrosequencing chip", NNIN REU Research Accomplishments, 2005, pp. 130-131.
Shepherd, L. et al., "A biochemical translinear principle with weak inversion ISFETs", *IEEE Trans Circuits Syst-I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .* , 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, pp. 5354-5361.

(56) References Cited

OTHER PUBLICATIONS

Simonian, A. L. et al., "FET bases biosensors for the direct detection of organophosphate neurotoxins", *Electroanalysis*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenylnaphthalene Dimide as the Electrochemically Active Ligand", *Anal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

Truman, P., "Monitoring liquid transport and chemical composition in lab on . . . ", *Lab on a Chip*, vol. 6, 2006, pp. 1220-1228.

Uslu, F. et al., "Labelfree fully electronic nucleic acid detection system based on a field-effect transistor device", *Biosens & Bioelectron*, vol. 19(12), 2004, pp. 1723-1731.

Van Der Wouden, E. et al., "Directional flow induced by synchronized longitudinal and zeta-potential controlling AC-electrical fields", *Lab Chip*, vol. 6(10), 2006, pp. 1300-1305.

Van Hal, R.E.G. et al., "A general model to describe the electrostatic potential at electrolyte oxide interfaces", *Advances in Colloid and Interface Science*, vol. 69, 1996, pp. 31-62.

Van Kerkhof, J et al., "The ISFET based heparin sensor with a monolayer of protamine as affinity ligand", *Biosensors & Bioelectronics*, vol. 10(3), 1995, pp. 269-282.

Van Kerkhof, J. et al., "ISFET Responses on a stepwise change in electrolyte concentration at constant pH", *Sensors Actuators B: Chemical*, vol. 18-19, Mar. 1994, pp. 56-59.

Van Kerkhof, J., "The Development of an ISFET-based Heparin Sensor", *Thesis*, 1994.

Wagner, T et al., ""All-in-one" solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proc. of the Natl. Acad. of Sciences (PNAS)*, vol. 102(9), 2005, pp. 3208-3212.

Woias, P., "Modelling the short time response of ISFET sensors", *Sensors and Actuators B*, vol. 24-25, 1995, pp. 211-217.

Woias, P. et al., "Slow pH response effects of silicon nitride ISFET sensors", *Sensors and Actuators B*, vol. 48, 1998, pp. 501-504.

Wu, P. et al., "DNA and protein microarray printing on silicon nitride waveguide surfaces", *Biosensens Bioelectron*, vol. 21(7), 2006, pp. 1252-1263.

Xu, J-J et al., "Analytical Aspects of FET-Based Biosensors", *Frontiers in Bioscience*, Oct. 2005, pp. 420-430.

Yeow, T.C.W. "A very large integrated pH-ISFET sensor array chip compatible with standard CMOS processes", *Sensor and Actuators B*, vol. 44, 1997, pp. 434-440.

Yuqing, M. et al., "Ion sensitive field effect trnasducer-based biosensors", *Biotechnology Advances*, vol. 21, 2003, 527-534.

Zhang, X et al. "32-Channel Full Customized CMOS Biosensor Chip for Extracellular neural Signal Recording", *Proceedings of the 2nd International IEEE EMBs Conference on Neural Engineering*, Arlington, VA-, 2005, pp. v-viii.

Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.

\* cited by examiner

US 8,673,627 B2

APPARATUS AND METHODS FOR PERFORMING ELECTROCHEMICAL REACTIONS

This application is a continuation-in-part of U.S. patent applications Ser. Nos. 12/474,897 and 12/475,311, both filed 29 May 2009, and claims priority therefrom and from U.S. provisional patent application Ser. No. 61/306,924 filed 22 Feb. 2010, all of the foregoing being incorporated by reference in their entireties.

BACKGROUND

Electrochemical detection is attractive because it provides high sensitivity, small dimensions, low cost, fast response, and compatibility with microfabrication technologies, e.g. Hughes et al, Science, 254: 74-80 (1991); Mir et al, Electrophoresis, 30: 3386-3397 (2009); Trojanowicz, Anal. Chim. Acta, 653: 36-58 (2009); Xu et al, Talanta, 80: 8-18 (2009); and the like. These characteristics have led to the development of a variety of sensors based on amperometric, potentiometric or impedimetric signals and their assembly into arrays for chemical, biochemical and cellular applications, e.g. Yeow et al, Sensors and Actuators B 44: 434-440 (1997); Martinoia et al, Biosensors & Bioelectronics, 16: 1043-1050 (2001); Hammond et al, IEEE Sensors J., 4: 706-712 (2004); Milgrew et al, Sensors and Actuators B 103: 37-42 (2004); Milgrew et al, Sensors and Actuators B, 111-112: 347-353 (2005); Hizawa et al, Sensors and Actuators B, 117: 509-515 (2006); Heer et al. Biosensors and Bioelectronics, 22: 2546-2553 (2007); Barbaro et al, Sensors and Actuators B, 118: 41-46 (2006); Anderson et al, Sensors and Actuators B, 129: 79-86 (2008); Rothberg et al, U.S. patent publication 2009/0127589; Rothberg et al, U.K. patent application GB24611127; and the like. In particular, several of these developments involve the use of large-scale arrays of electrochemical sensors for monitoring multiple reaction steps on a large plurality of analytes confined to such an array, e.g. Anderson et al (cited above); Rothberg et al (cited above); and the like. Typically in such systems, analytes are randomly distributed among an array of confinement regions, such as microwells or reaction chambers, and reagents are delivered to such regions by a fluidics system that directs flows of reagents through a flow cell containing the sensor array. Microwells in which reactions take place, as well as empty wells where no reactions take place, may be monitored by one or more electronic sensors associated with each of the microwells.

Such systems are subject to a host of interrelated phenomena that make highly sensitive measurements challenging, particularly under low signal conditions. Such phenomena include unstable reference voltage for the electrical sensors, lack of knowledge as to which confinement regions contain analytes, variability in the amount of reagents delivered by a flow stream to analytes confined to different regions of an array potential mixing of successively delivered reagents, changes in instrument temperature, fluid leaks that may affect fluid potential, extraneous electrical interference, e.g. 60 Hz noise, cell phones, or the like, all of which may affect the quality of signals collected. In addition, for specific applications, there may further challenges related to particular reagents used, the sensitivity of a sensor for the analyte being measure, the presence or absence of interfering compounds, such as other reaction byproducts, and the like.

In view of the above, it would be advantageous to have available a system for carrying out multi-reagent electrochemical reactions in parallel on a large number of analytes which overcame the deficiencies of current approaches.

SUMMARY OF THE INVENTION

The present invention is directed to apparatus and methods for delivering multiple reagents to a plurality of reactions carried out on, and monitored by, a large-scale array of electronic sensors. In one aspect, such invention provides apparatus and methods for reducing noise in output signals generated by such electronic sensors in response to changes in reaction conditions. The present invention is exemplified in a number of implementations and applications, some of which are summarized below and throughout the specification.

In one aspect, the invention includes an apparatus for performing multi-step electrochemical reactions, wherein a stable reference voltage is provided through a reaction flow chamber to electronic sensors monitoring such multi-step electrochemical reactions. In one embodiment, the apparatus comprises (a) one or more reaction vessels each coupled to an electronic sensor for monitoring products in the reaction vessel, the electronic sensor generating an output signal related to a concentration or presence of a product, the output signal depending on a reference voltage; (b) a fluidics system for sequentially delivering a plurality of electrolytes to the reaction vessel one at a time and (c) a reference electrode in contact with a selected electrolyte of the plurality, the reference electrode being in fluid communication with the reaction chamber and providing the reference voltage to each electronic sensor without the reference electrode contacting any of the non-selected electrolytes. As described more fully below, in one embodiment, the one or more reaction vessels is an array of microwells disposed on an array of chemFET sensors which, in turn, is disposed in a flow cell in fluid communication with the microwells.

In another aspect, the invention includes an apparatus comprising a sensor array comprising floating gate ion-sensitive field-effect transistors, on which a flow path is defined by a flow cell, such that sensors of the array outside of the flow path are inactivated by electrically connecting their floating gates. In one aspect, such apparatus comprises (a) a sensor array comprising a plurality of sensors formed in a circuit-supporting substrate, each sensor of the array comprising a chemically sensitive field-effect transistor (chemFET) having a floating gate, the chemFET being configured to generate at least one electrical signal related to a concentration or presence of one or more reaction products proximate thereto and a microwell array disposed on the circuit-supporting substrate such that each microwell is disposed on at least one sensor, wherein one or more microwells contain analyte; and (b) a fluidics system for delivering reagents to the microwell array, the fluidics system comprising a flow cell having an inlet, an outlet and a flow chamber that defines a flow path of reagents as they pass from the inlet to the outlet, wherein the flow chamber is configured to deliver the reagents transversely over open portions of the microwells in the flow path, and wherein the floating gates of sensors outside of the flow path are electrically connected and held at a common voltage.

In another aspect, the invention include a method for locating analytes distributed among a plurality of microwells comprising the steps of (a) providing a plurality of microwells disposed on an array of sensors, wherein each microwell has an opening in fluid communication with a flow chamber and is capable of retaining at least one analyte, and wherein each microwell is disposed on at least one sensor configured to provide at least one output signal in response to reagents proximate thereto; (b) changing reagents in the flow chamber from a first reagent in response to which sensors generate a first output signal to a second reagent in response to which sensors to generate a second output signal; and (c) correlating a time delay of a second output signal from a sensor in response to said changing with the presence of an analyte in its corresponding microwell.

In a related aspect, the invention further includes an article of manufacture comprising a sensor array comprising a plurality of sensors formed in a circuit-supporting substrate, each sensor of the array being configured to generate at least one electrical signal related to a concentration or presence of one or more predetermined species proximate thereto and a microwell array disposed on the circuit-supporting substrate such that each microwell thereof has an opening on a surface of the microwell array and is disposed on at least one sensor; and a plurality of analytes randomly distributed in the microwells at locations determinable by an output signal generated by its corresponding sensor. In one embodiment, such analytes each comprise a particle having attached thereto a clonal population of a nucleic acid fragment, such as a genomic DNA fragment, cDNA fragment, or the like.

In another aspect, the invention provides a method of reducing noise in output signals from a sensor array related to reactions and/or analytes disposed in a microwell array. Such method comprises the steps of (a) disposing analyte onto the microwell array such that a portion of the microwells contain analyte; (b) obtaining an output signal generated by a microwell containing analyte or reaction byproduct; and (c) subtracting from such output signal an average of output signals from neighboring microwells that do not contain an analyte or a reaction byproduct.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

DETAILED DESCRIPTION

Figure 1A:
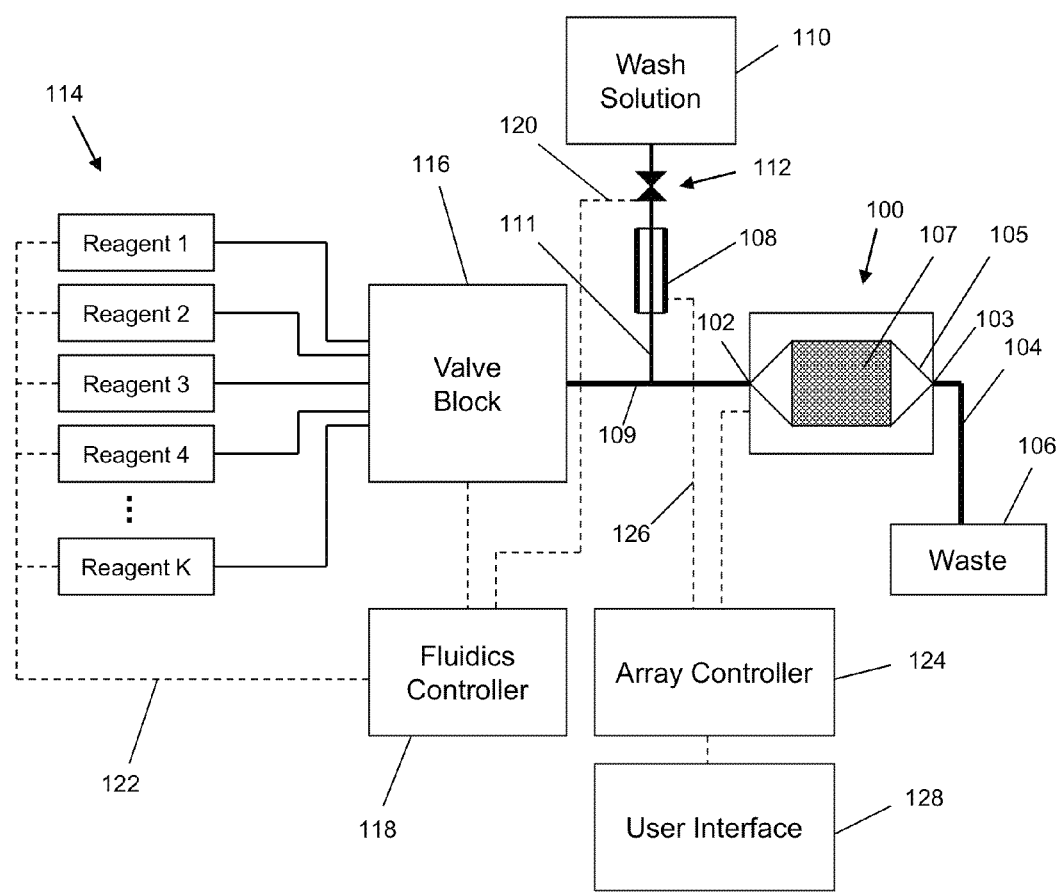
FIG. 1A illustrates components of one embodiment of the apparatus of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. For example, the microelectronics portion of the apparatus and array is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein. Guidance for making arrays of the invention is found in many available references and treatises on integrated circuit design and manufacturing and micromachining, including, but not limited to, Allen et al, CMOS Analog Circuit Design (Oxford University Press, $2^{nd}$ Edition, 2002); Levinson, Principles of Lithography, Second Edition (SPIE Press, 2005); Doering and Nishi, Editors, Handbook of Semiconductor Manufacturing Technology, Second Edition (CRC Press, 2007); Baker, CMOS Circuit Design, Layout, and Simulation (IEEE Press, Wiley-Interscience, 2008); Veendrick, Deep-Submicron CMOS ICs (Kluwer-Deventer, 1998); Cao, Nanostructures & Nanomaterials (Imperial College Press, 2004); and the like, which relevant parts are hereby incorporated by reference. Likewise, guidance for carrying out electrochemical measurements of the invention is found in many available references and treatises on the subject, including, but not limited to, Sawyer et al, Electrochemistry for Chemists, $2^{nd}$ edition (Wiley Interscience, 1995); Bard and Faulkner, Electrochemical Methods: Fundamentals and Applications, $2^{nd}$ edition (Wiley, 2000); and the like, which relevant parts are hereby incorporated by reference.

In one aspect the invention is directed to apparatus and methods for carrying out and monitoring a plurality of multi-step reactions with electronic sensors. The multi-step reactions may be cyclic, such as in DNA sequencing reactions, DNA synthesis reactions, or the like, where repeated cycles of one or more steps are carried out, or they may be non-cyclic, such as in multi-component labeling reactions, as for example, in a sandwich assay using enzymatic labels. Multi-step reactions may also result from the presence of a biological material, such as living cells or tissue sample, where responses, e.g. the presence or absence of metabolites, are detected in response to a series of reagent exposures, which may be drug candidate molecules, or the like. Preferably, electronic sensors of the invention are integrated into a sensor array suitable for sensing individual reactions taking place on or adjacent to a surface of the array. In one embodiment, an array of reaction confinement regions is integral with such a sensor array. An array of reaction confinement regions may take the form of a microwell array or a reaction chamber array made by conventional micro- or nanofabrication techniques, for example, as described in Rothberg et al, U.S. patent publication US2009/0127589 and Rothberg et al, U.K. patent application GB24611127. In one embodiment, each microwell or reaction chamber in such an array has at least one sensor that is in a sensing relationship so that one or more characteristics of a reaction in the microwell or reaction chamber can be detected or measured. Typically electronic sensors of the invention measure directly or indirectly (for example, by the use of a binding compound or label) reaction byproducts including, but not limited to, chemical species resulting from a reaction or physical changes caused by a reaction, such as increases or decreases in temperature, e.g. as disclosed in Rothberg et al (U.S. and U.K. patent publications cited above). Preferably, electronic sensors of the invention convert changes in the presence, concentration or amounts of reaction byproducts into an output signal, which may be a change in a voltage level or a current level which, in turn, may be processed to extract information about a reaction. Electronic sensors of the array, or a subset of such sensors, may also be used to monitor the presence or concentration of reactants, indicator molecules, or other reagents, such as reagents for identifying microwells containing analytes (described more fully below). The structure and/or design of sensors for use with the invention may vary widely, as exemplified by the following references, which are incorporated by reference: Rothberg et al, U.S. patent publication US2009/0127589; Rothberg et al, U.K. patent application GB2461 1127; Barbaro et al, U.S. Pat. No. 7,535,232; Sawada et al, U.S. Pat. No. 7,049,645; Kamahori et al, U.S. patent publication 2007/0059741; Miyahara et al, U.S. patent publications 2008/0286767 and 2008/0286762; O'uchi, U.S. patent publication 2006/0147983; Osaka et al, U.S. patent publication 2007/0207471; Esfandyarpour et al, U.S. patent publication 2008/0166727; and the like. In a preferred embodiment, sensors of the array comprise at least one chemically sensitive field effect transistor that is configured to generate at least one output signal related to a property of a chemical reaction in proximity thereof. Such properties may include a concentration (or a change in concentration) of a reactant or product, or a value of physical property (or a change in such value), such as temperature. Desirable configurations and physical characteristic of electronic sensor arrays and microwell arrays are described more fully below. In one embodiment of such sensor arrays, the chemFETs of the sensors include a floating gate. In another embodiment of the invention, electronic sensors of the array each generate an output signal that depends in part on the value of the voltage of a reference electrode that is in fluid contact with microwell array. In particular embodiments, a single reference electrode is provided so that each sensor generates output signals with the same reference voltage.

Components of one embodiment of the invention are illustrated diagrammatically in FIG. 1A. Flow cell and sensor array (100) comprise an array of reaction confinement regions (which may comprise a microwell array) that is operationally associated with a sensor array, so that, for example, each microwell has a sensor suitable for detecting an analyte or reaction property of interest. Preferably, a microwell array is integrated with the sensor array as a single chip, as explained more fully below. A flow cell can have a variety of designs for controlling the path and flow rate of reagents over the microwell array. In some embodiments, a flow cell is a microfluidics device. That is, it may be fabricated with micromachining techniques or precision molding to include additional fluidic passages, chambers, and so on. In one aspect, a flow cell comprises an inlet (102), an outlet (103), and a flow chamber (105) for defining the flow path of reagents over the microwell array (107). Embodiments of the flow cell are described more fully below. Reagents are discarded into a waste container (106) after exiting flow cell and sensor array (100). In accordance with the invention, a function of the apparatus is to deliver different reagents to flow cell and sensor array (100) in a predetermined sequence, for predetermined durations, at predetermined flow rates, and to measure physical and/or chemical parameters in the microwells that provide information about the status of a reaction taking place therein, or in the case of empty wells, information about the physical and/or chemical environment in the flow cell. To this end, fluidics controller (118) controls by lines (120 and 122) the driving forces for a plurality of reagents (114) and the operation of valves (for example, 112 and 116) by conventional instrument control software, e.g. Lab View (National Instruments, Austin, Tex.). The reagents may be driven through the fluid pathways, valves and flow cell by pumps, by gas pressure, or other conventional methods. In embodiments where a single reference electrode (108) is positioned upstream of flow cell and sensor array (100), preferably a single fluid or reagent is in contact with reference electrode (108) throughout an entire multi-step reaction. This is achieved with the configuration illustrated in FIG. 1A where reagents 1 through K (114) are directed through passage (109) to flow cell (105). When those reagents are flowing, valve (112) is shut, thereby preventing any wash solution from flowing into passage (109). Although the flow of wash solution is stopped, there is still uninterrupted fluid and electrical communication between reference electrode, passage (109), and sensor array (107). At most reagents 1 through K when flowing through passage (109) diffuse into passage (111), but the distance between reference electrode (108) and the junction between passages (109) and (111) is selected so that little or no amount of the reagents flowing in common passage (109) reach reference electrode (108). Although FIG. 1A and other figures illustrate an electrode (for example, reference electrode, 108) as a cylinder concentric with a fluid passage (for example, 111), reference electrodes, such as (108), may have a variety of different shapes. For example, it could be a wire inserted into the lumen of (111). In one aspect, reference electrode (108) constitutes a section of passage (112) that is made of a conductive material, such as stainless steel, gold, or the like. Preferably the material is inert with respect to reagents in contact with it. Reference electrode (108) in one embodiment is a tube made of a conductive material which forms part of passage (112). Generally in the figures, whenever electrodes are represented as a cylinder concentric with a flow path, such figure clement is intended to comprise electrodes having a variety of configurations, as noted, but with a preferred configuration as a tube of conductive material enclosing part of a flow path.

The value of the reference voltage depends on the interface between the electrode and the solution in which the electrode is in contact. It has been observed and appreciated that (for example) solutions of different nucleoside triphosphate cause the reference voltage to change, thereby causing undesirable changes in the output signals of the sensors. For multi-step reactions using frequent wash steps, wash solution (110) may be selected as the reagent in continuous contact with reference electrode (108) as illustrated in FIG. 1A. (That is, the wash solution would be the "selected electrolyte" or "selected reagent" and the dNTP reagents would be the "non-selected electrolytes" or "non-selected reagents" as the terms are used elsewhere herein). As further described below, in certain DNA sequencing methods washes are implemented after each introduction of nucleoside triphosphates; thus, in such methods a wash solution is preferably in continuous contact with reference electrode. Such contact may be obtained by including a reservoir for holding the selected electrolyte, such as the wash solution, which is connected by a branch passage (e.g. 111) to a common passage (e.g. 109) for delivering electrolytes to a reaction vessel. In one aspect, the branch passage has a valve disposed between the reservoir (e.g., 110) and a junction with the common passage, wherein the reference electrode is disposed in the branch passage between the valve and the junction such that the reference electrode is in fluid communication with the reaction vessel and such that whenever the valve (e.g. 112) is shut and fluid within the branch passage is stationary, substantially no non-selected electrolyte contacts the reference electrode. The only transfer of non-selected electrolyte into the branch passage is by diffusion; thus, the reference electrode may be place sufficiently far away from the junction so that minimal or no non-selected electrolyte reaches it during the time the selected electrolyte is stationary.

Further components of this embodiment include array controller (124) for providing bias voltages and timing and control signals to the sensor array (if such components are not integrated into the sensor array), and for collecting and/or processing output signals. Information from flow cell and sensor array (100), as well as instrument settings and controls may be displayed and entered through user interface (128). For some embodiments, for example, nucleic acid sequencing, the temperature of flow cell and sensor array (100) is controlled so that reactions take place and measurements are made at a known, and preferably, a predetermined temperature. Such temperature may be controlled by conventional temperature control devices, such as, a Peltier device, or the like. In one aspect, temperature is conveniently controlled by controlling the temperatures of the reagents flowing through the flow cell. Noise in output signals due to temperature differences within an array or due to temperature fluctuations may be recorded by temperature reference sensors within the array, as described in Rothberg et al (published patent application cited above). Such noise may then be subtracted from the output signal in conventional signal processing techniques.

Figure 2A:
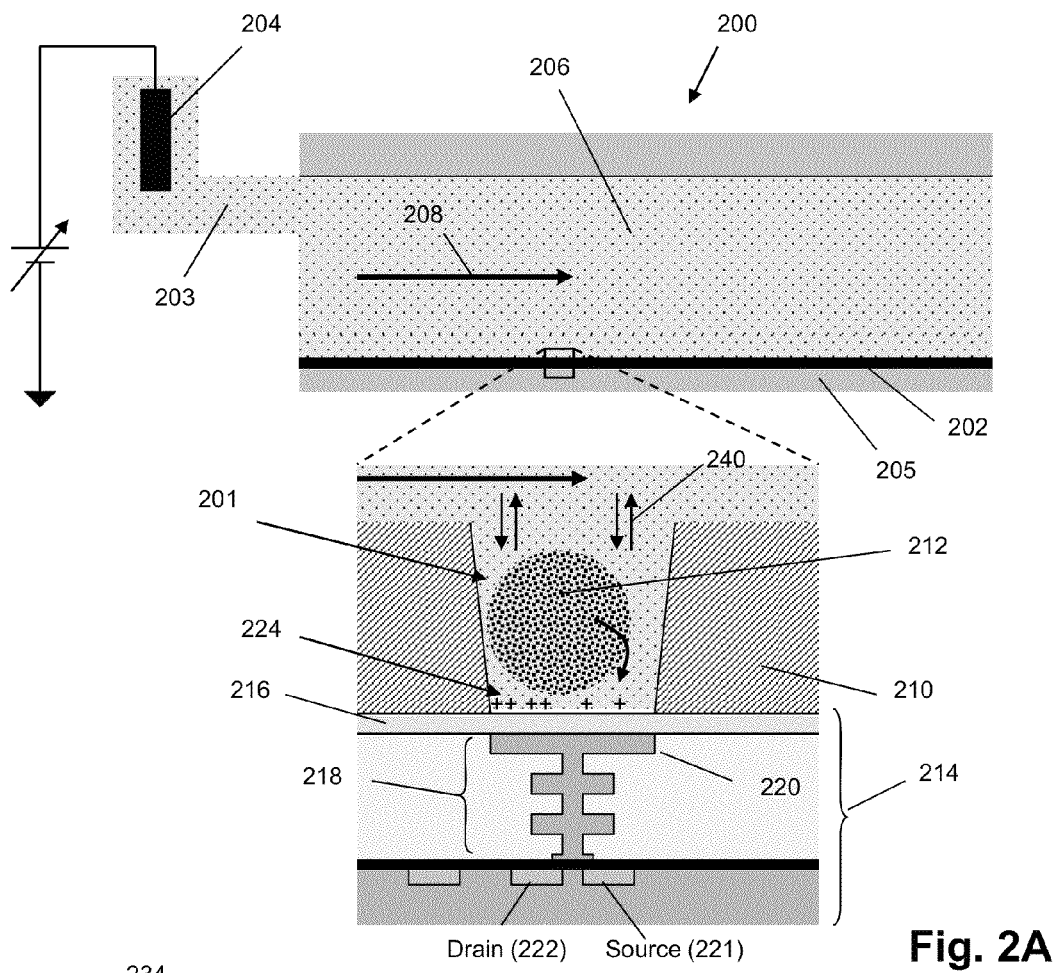
FIG. 2A illustrates a section of a flow cell with an external reference electrode and enlargement of an exemplary electronic sensor.

FIG. 2A is an expanded and cross-sectional view of flow cell (200) showing a portion (206) of a flow chamber with reagent flow (208) moving across the surface of microwell array (202) over the open ends of the microwells. Preferably, microwell array (202) and sensor array (205) together form an integrated unit forming a bottom wall or floor of flow cell (200). In one embodiment, reference electrode (204) is fluidly connected to flow chamber (206). A microwell (201) and sensor (214) are shown in an expanded view. Microwell (201) may be formed by conventional microfabrication technique, as described briefly below. Microwell volume, shape, aspect ratio (such as, base width-to-well depth ratio), and the like, are design choices that depend on a particular application, including the nature of the reaction taking place, as well as the reagents, byproducts, and labeling techniques (if any) that are employed. Sensor (214) is a chemFET with floating gate (218) having sensor plate (220) separated from the microwell interior by passivation layer (216). Sensor (214) is predominantly responsive to (and generates an output signal related to) the amount of charge (224) present on the passivation layer (216) opposite of sensor plate (220). Changes in charge (224) cause changes in the current between source (221) and drain (222) of the FET, which may be used directly to provide a current-based output signal or indirectly with additional circuitry to provide a voltage output signal. Reactants, wash solutions, and other reagents move into microwells from flow chamber (206) primarily by diffusion (240).

Typically reactions carried out in microwells (202) are analytical reactions to identify or determine characteristics or properties of an analyte of interest. Such reactions generate directly or indirectly byproducts that affect the amount of charge adjacent to sensor plate (220). (Indirect detection may occur, for example, if byproduct chelators or other binding compounds are used that affect the sensor after binding an analyte of interest, or if labeling moieties are employed, such as enzymes that may generate a secondary byproduct as the result of a binding event, or the like) If such byproducts are produced in small amounts or rapidly decay or react with other constituents, then multiple copies of the same analyte may be analyzed in microwell (201) at the same time in order in increase the output signal ultimately generated. In one embodiment, multiple copies of an analyte may be attached to solid phase support (212), either before or after deposition into a microwell. Solid phase supports (212) may include microparticles, nanoparticles, beads, solid and porous, comprising gels, and the like. For nucleic acid analytes, multiple, connected copies may be made by rolling circle amplification (RCA), exponential RCA, and like techniques, to produce an amplicon without the need of a solid support.

Figure 2B:
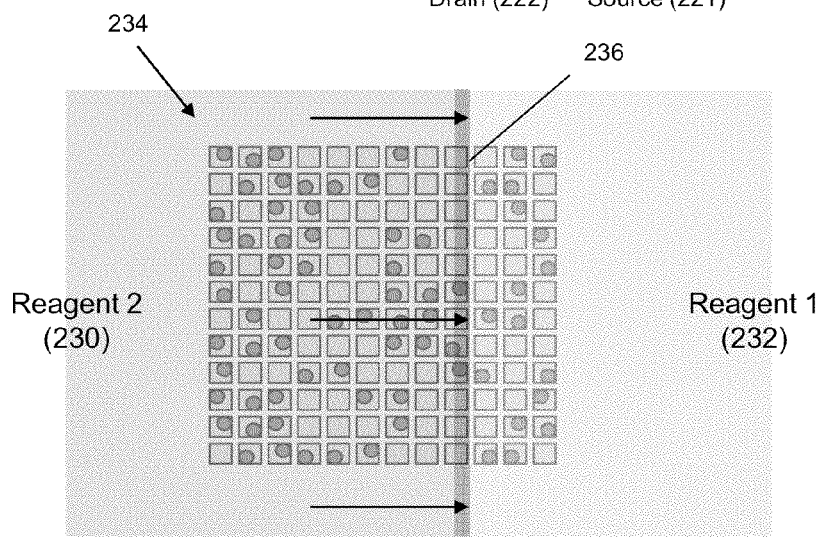
FIG. 2B illustrates the movement of two successive reagents over a section of a microwell array with an ideally uniform flow front between the different reagents.

As mentioned above, in one aspect, flow cells of the invention constrain reagents to move transversely in a laminar flow over a microwell array. The rate of flow is a design choice depending on the nature of the reactions carried out, the geometry and size of the flow chamber and microwell array, and the like. Generally, however, when different reagents are successively delivered to the microwells, a flow cell delivers each new reagent flow with a uniform flow front as it transits the flow chamber during the switch from one reagent to another. That is, flow cell design and reagent flow rate are selected so that as one reagent follows another with little or no mixing occurring at the boundary between the successive fluids. FIG. 2B illustrates a uniform flow front between two reagents moving across section (234) of a microwell array. A "uniform flow front" means that successive reagents, e.g. reagent 1 (232) and reagent 2 (230), undergo little or no mixing as the reagents move across the microarray, thereby keeping boundary (236) between reagent 1 (232) and reagent 2 (230) narrow as it moves across a microarray. Such boundaries may be linear for flow cells having inlets and outlets at opposite ends of their flow chambers, or such boundaries may be curvilinear for flow cells having central inlets (or outlets) and peripheral outlets (or inlets).

Reference Electrodes for Electronic Sensor Arrays

The fluid-electrode interface influences the way the reference potential is transmitted into the fluid. That is, the interface potential between the fluid and the electrode fluctuates with the composition of the fluid (which may be somewhat turbulent and inhomogeneous), introducing a voltage offset to the potential of the bulk fluid which varies with time and possibly location, as well. Considerably greater reference potential stability may be achieved by moving the location of the reference electrode so that it is substantially isolated from changes in fluid composition. This may be accomplished by introducing a conductive solution of a consistent composition over at least part of the surface of the electrode (hereafter the "electrode solution" or "selected electrolyte"), arranging the electrode to avoid it coming into direct contact with the changing fluids in the flow cell and, instead, arranging the electrode solution (not the electrode) to come into electrical contact with the fluid in the flow cell. The result is a transfer of the reference potential to the flow cell solution (be it a reagent or wash or other solution) that is considerably more stable than is obtained by direct insertion of an electrode into the flow cell solution. We refer to this arrangement as a liquid-liquid or fluid-fluid reference electrode interface. The fluid-fluid interface may be created downstream from the flow cell, upstream from the flow cell (as exemplified in FIG. 1A), or in the flow cell. Examples of such alternative embodiments are shown in FIGS. 1B-1E.

Figure 1B:
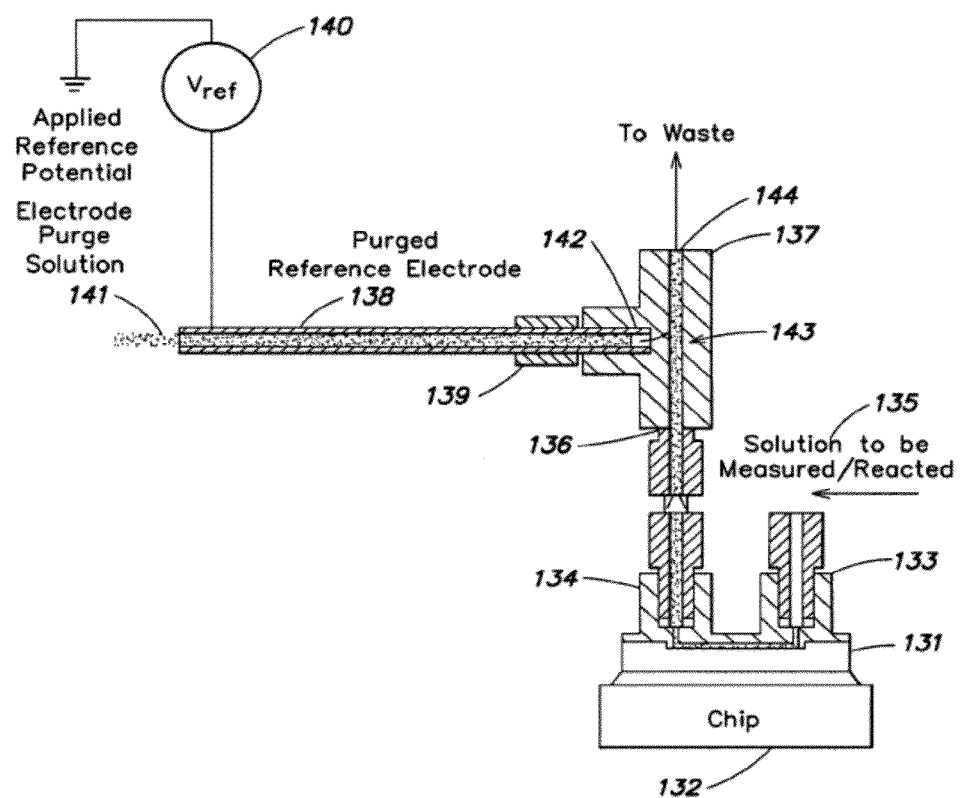
FIG. 1B is a diagrammatic illustration of a cross-section of a first example of a fluid-fluid reference electrode interface in which the reference electrode is introduced downstream in the reagent path from the flow cell.

Turning first to FIG. 1B, there is shown a diagrammatic illustration of an embodiment in which the fluid-fluid interface is created downstream from the flow cell. In this example, the flow cell apparatus 131 is, as above, mounted on a chip 132 which contains the sensor array (not shown). The flow cell apparatus includes an inlet port 133 and an outlet port 134. That is, the reagent fluids are introduced into port 133 via conduit 134 and they exit via port 134. A first port 136 of a fluid "Tee" connector 137 is coupled onto flow cell outlet port 134 via conventional couplings to receive the fluid exiting from the flow cell. A reference electrode such as a hollow electrically conductive tube 138 is fed into another port of the Tee connector via a fluid-tight coupling 139. The reference electrode is connected to a reference potential source 140 and a suitable electrode solution 141 is flowed into the center bore of the electrode tube.

Two modes of operation are possible. According to a first mode, the electrode solution may be flowed at a rate that is high enough to avoid back flow or diffusion from the fluid flowing out of the flow cell. According to a second mode, once the electrode solution has filled the electrode and come into contact with the outlet flow from the flow cell, a valve (not shown) may be closed to block further flow of the electrode solution into the electrode and, as the electrode solution is an incompressible liquid, there will be substantially no flow into or out of the electrode, yet the fluid-fluid interface will remain intact. This presumes, of course an absence of bubbles and other compressible components. For a fluid-fluid interface to take the place of a metal-fluid interface, the tip 142 of the electrode 138 is positioned to stop within the Tee connector short of the fluid flow out of the flow cell, so that it is the "electrode solution," not the electrode itself, that meets the outlet flow from the flow cell, indicated at 143, and carries the reference potential from the electrode to the reagent solution exiting the flow cell. The two fluid streams interact in the Tee connector at 143 and if the electrode solution is flowing, it flows out the third port 144 of the Tee connector with the reagent flow, as a waste fluid flow, for disposal. This approach eliminates interfacial potential changes at the electrode surface. Using a fluid-fluid interface to convey a stable reference potential from a reference electrode to a flow cell, various alternative embodiments are possible.

Figure 1C:
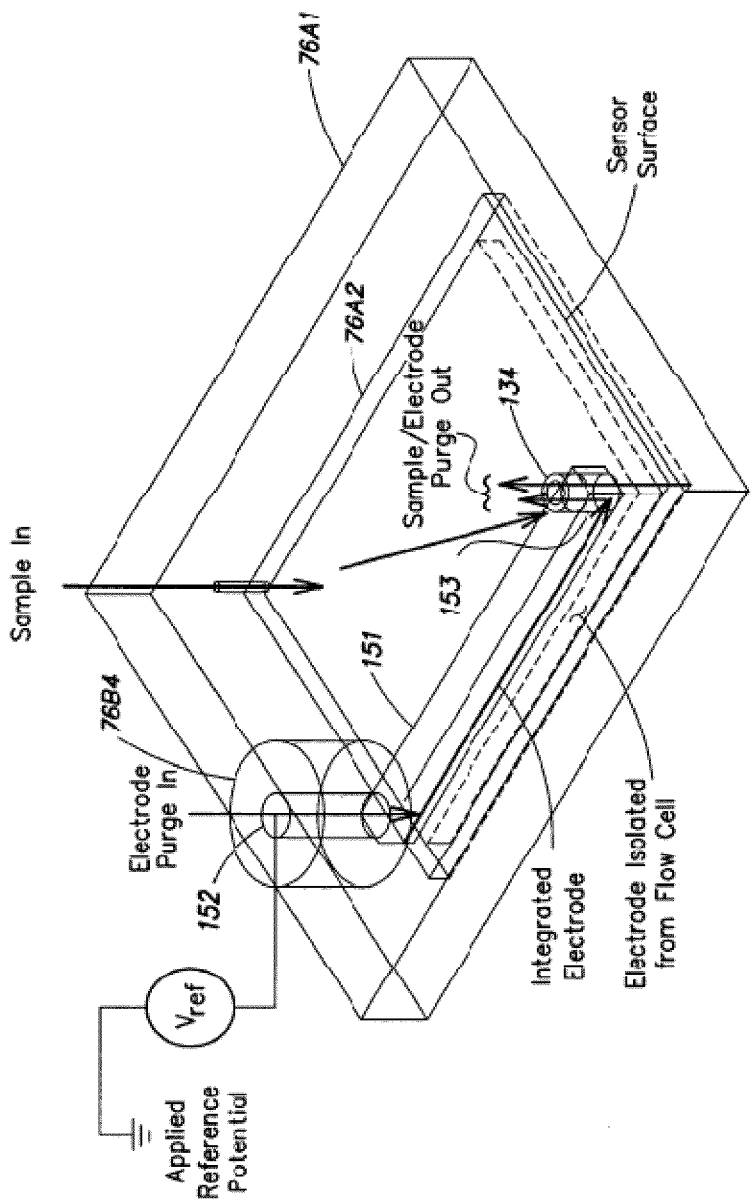
FIGS. 1C and 1D are diagrammatic illustrations of two alternative examples of ways to construct apparatus to achieve the fluid-fluid interface of FIG. 1B.

In one alternative, illustrated in FIG. 1C, the referencing junction (i.e., the fluid-fluid interface) can be moved into the structure of the members forming the flow cell or even into the sensor chip itself, but with the electrode solution never entering the flow cell. For example, a manifold 151 may be formed in the flow cell assembly outside the flow chamber itself, having an inlet 152 for receiving electrode solution and an outlet 153 in fluid communication with the flow cell's outlet conduit 134. The electrode may be a separate element disposed in the manifold or it may be a metallization applied to an interior surface of the manifold.

Alternatively, the manifold can be formed in the substrate of the chip itself by fabricating in the substrate a hollow region which can serve as a conduit allowing fluid passage from an inlet end to an outlet end. An electrode may be inserted therein via a separate inlet port 152 or part of the (interior or exterior, as appropriate) surface of the conduit may be metalized during fabrication, to serve as the electrode. The flow path for reagent fluid to exit the flow chamber may include a conduit portion and the electrode conduit/manifold may deliver electrode solution to the reagent fluid outlet conduit, wherein the two fluids come into contact to provide the fluid-fluid interface that applies the reference electrode voltage to the flow cell.

In each instance, the electrode may be hollow and have the electrode solution delivered through its interior, or the electrode solution may be delivered over the exterior of the electrode. For example, as shown in FIG. 1C, the electrode may be hollow, such as being the interior surface of the manifold 151, and it may have an exterior that is insulated from the flow cell using any suitable structure and material (not shown, to avoid obfuscation of the basic idea).

The electrode assembly thus may be built into the sensor chip itself or into the flow cell or its housing, coupled with a fluid inlet through which electrode solution may be introduced. The flow path for reagent fluid to exit the flow chamber may include a conduit portion 134 into which the electrode solution is presented, and wherein the two fluid flows come into contact to provide the fluid-fluid interface. The electrode solution may flow or be static.

Figure 1D:
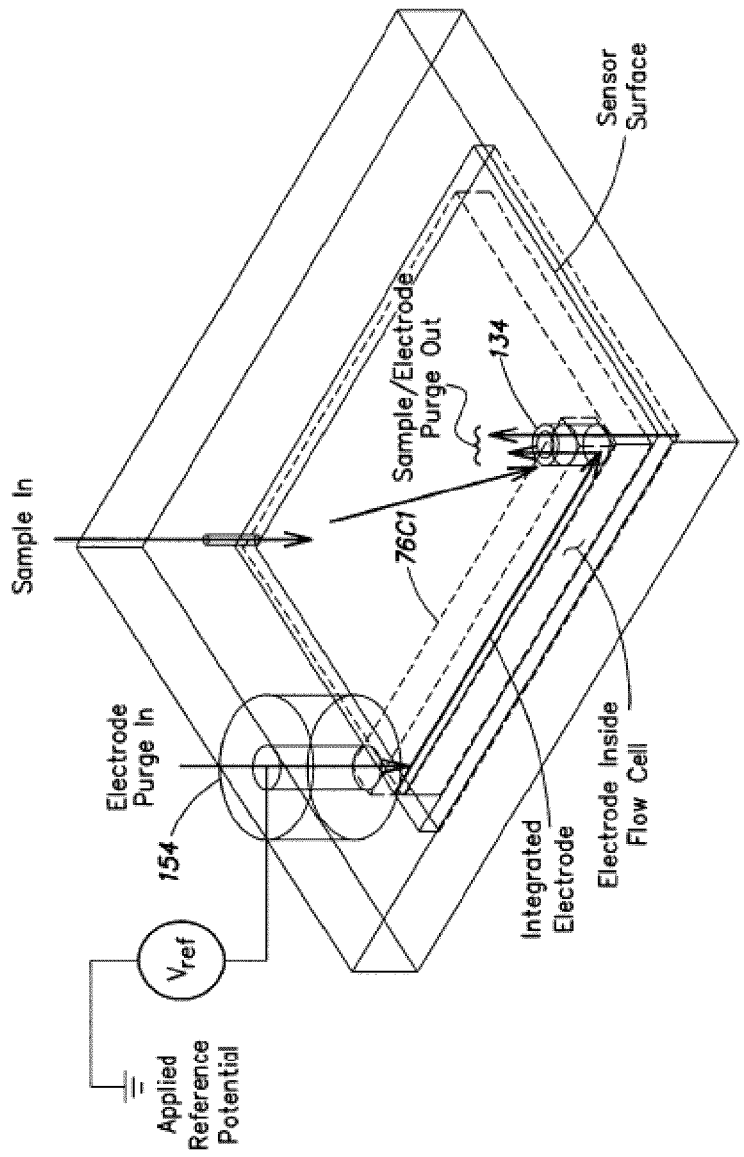
Figure 1E:
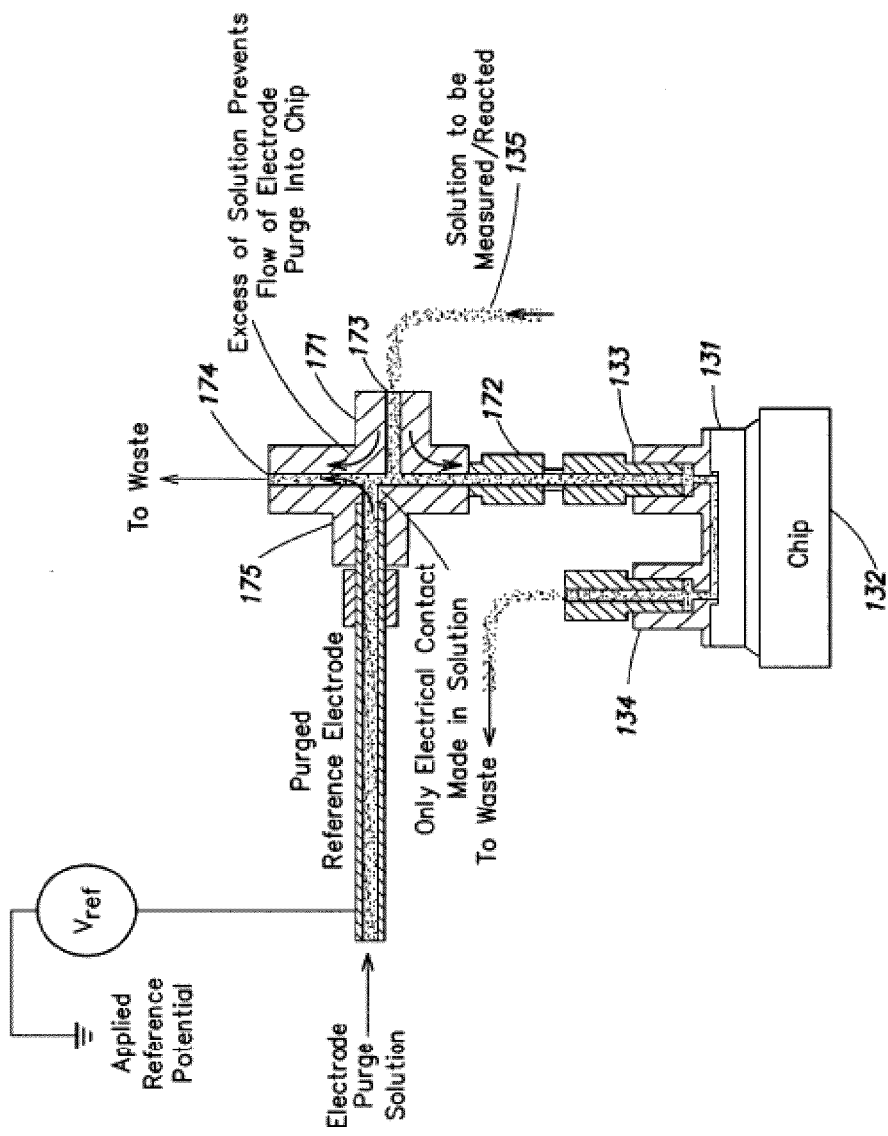
FIG. 1E is a diagrammatic illustration of a cross-section of a second example of a fluid-fluid reference electrode interface in which the reference electrode is introduced upstream in the reagent path from the flow cell.

As a further alternative embodiment, depicted in FIG. 1D, the electrode structure may be integrated into or disposed within the flow cell itself. This may be done in two distinctly different ways. First, the electrode solution may be introduced into the flow chamber and flowed from an inlet 154 into the flow cell (provided for that purpose) to an outlet port 134 through which both the electrode solution and the reagent flow exit the flow chamber. If both fluids are arranged to move through the chamber in a laminar flow, they will not intermix (or there will be little mixing and interaction) until they reach the outlet. So there need not be a barrier between the two fluids. Their entire region of contact will be the locus of fluid-fluid interfacing, which may provide considerably more surface for that interface than the other illustrated alternatives. Second, a fluid conduit may be provided adjacent to the flow chamber or even fully or partly within the flow chamber, with a non-conductive exterior. The electrode may extend along the interior of the conduit, between an electrode fluid inlet and a fluid outlet that permits the electrode solution to interface with the reagent flow, such as in a common outlet conduit 134.

In the foregoing examples, the reference potential is introduced either in or downstream of the flow cell. However, the same approach is possible with the electrode provided upstream of the flow cell, as shown diagrammatically in FIG. 1E. There, 133 is the inlet port to the flow cell and 134 is the outlet port, as in FIG. 1B. A cross-connector 171 having four ports has a first port 172 coupled onto the inlet port. A second port, 173, receives the solution to be reacted or measured (e.g., a reagent) via inlet conduit 135. A third port, 174, is used as a waste outlet port. The fourth port, 175, receives the electrode in the same manner as previously shown in FIG. 1B. Within the cross-connector, the electrode solution and the solution to be reacted/measured interact to transmit the reference potential into the flow cell. In contrast with some of the other alternative embodiments, however, at least some implementations of this embodiment may require that the solution to be measured/reacted must have a sufficiently high flow rate as to prevent flow of the electrode solution into the flow chamber. However, with judicious configuring of the cross-connector, it may still be possible to avoid the need to flow electrode solution continuously.

Use of Electronic Sensors to Locate Analytes in Microwells

Figure 3A:
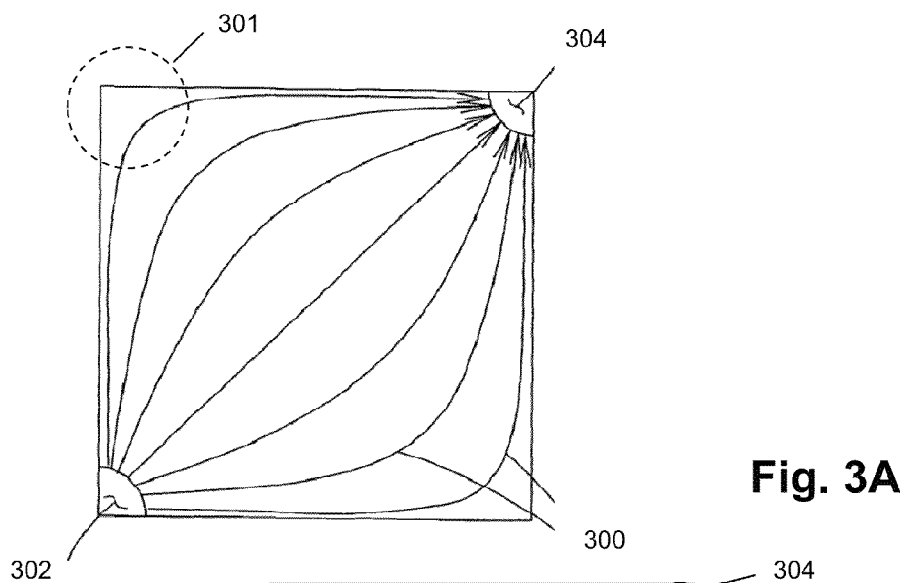
FIG. 3A is a diagram illustrating flow paths through a flow chamber having diagonally opposed inlet and outlet.

In one aspect of the invention, electronic sensors are used to locate microwells that contain analyte and/or particles and microwells that are empty. Such a process is useful because output signals from empty wells allows the estimation of common noise components that may be subtracted from output signals measured from analyte-containing microwells, thereby improving signal-to-noise ratios. Moreover, in many embodiments analytes and/or particles are randomly disposed in microwells by placing them in solution and flowing them into the flow chamber where they settle randomly into microwells, as illustrated in FIG. 3A, and further exemplified in Rothberg et al (U.S. patent publication cited above); thus, a method of electronically identifying which microwells contain analyte and which are empty is needed.

Usually, only a single analyte is disposed in a single microwell. In one aspect, multiple copies of the same analyte are attached to solid support, such as a bead or particle, which, in turn, is selected to match a microwell in size and shape so that only a single solid support fits into a single microwell, thereby ensuring only one kind of analyte is in a single microwell. As mentioned above, for some types of analytes, such as nucleic acids, methods are available, such as rolling circle amplification (RCA), or the like, to construct connected amplicons that form a single body that may exclusively occupy a microwell, e.g. as disclosed in Drmanac et al, U.S. patent publication 2009/0137404. Mier the random distribution of analytes into microwells, electronic sensors responsive to changes in surface charge may be used to identify microwells containing analyte. Thus, in one aspect, a method of the invention includes introducing a sensor-active reagent, which may be the same or different as a reagent used in an analytical process of interest, which is capable of altering the charge adjacent to a sensor as a function of its concentration.

In one embodiment, this aspect of the invention may comprise the following steps: (a) changing reagents in a flow chamber from a first reagent that sensors generate in response thereto a first output signal to a second reagent that sensors to generate in response thereto a second output signal; and (b) correlating a time delay in the generation of a second output signal by a sensor in response to said changing with the presence of an analyte in its corresponding microwell. Any type of electrochemical sensor may be used in this aspect of the invention, including a potentiometric sensor, an impedimetric sensor, or an amperometric sensor, so long as the output signal depends on the interaction of an electrode or other analyte-sensitive surface and the sensor-active reagent whose arrival is delayed by physical or chemical obstructions in a microwell. In one embodiment, the sensor-active reagent is a wash solution at a different pH than the reagent it replaces, which may also be the wash solution. The step of changing reagents includes recording the output signals of the sensors in the array so that a continuous time record of signal values (or a digital representation thereof) is obtained which can be analyzed to determine the timing of changes in output signals that correspond to the times at which the sensor-active reagent reach the respective sensors. Such data recording and analysis may be carried out by conventional data acquisition and analysis components.

Figure 2C:
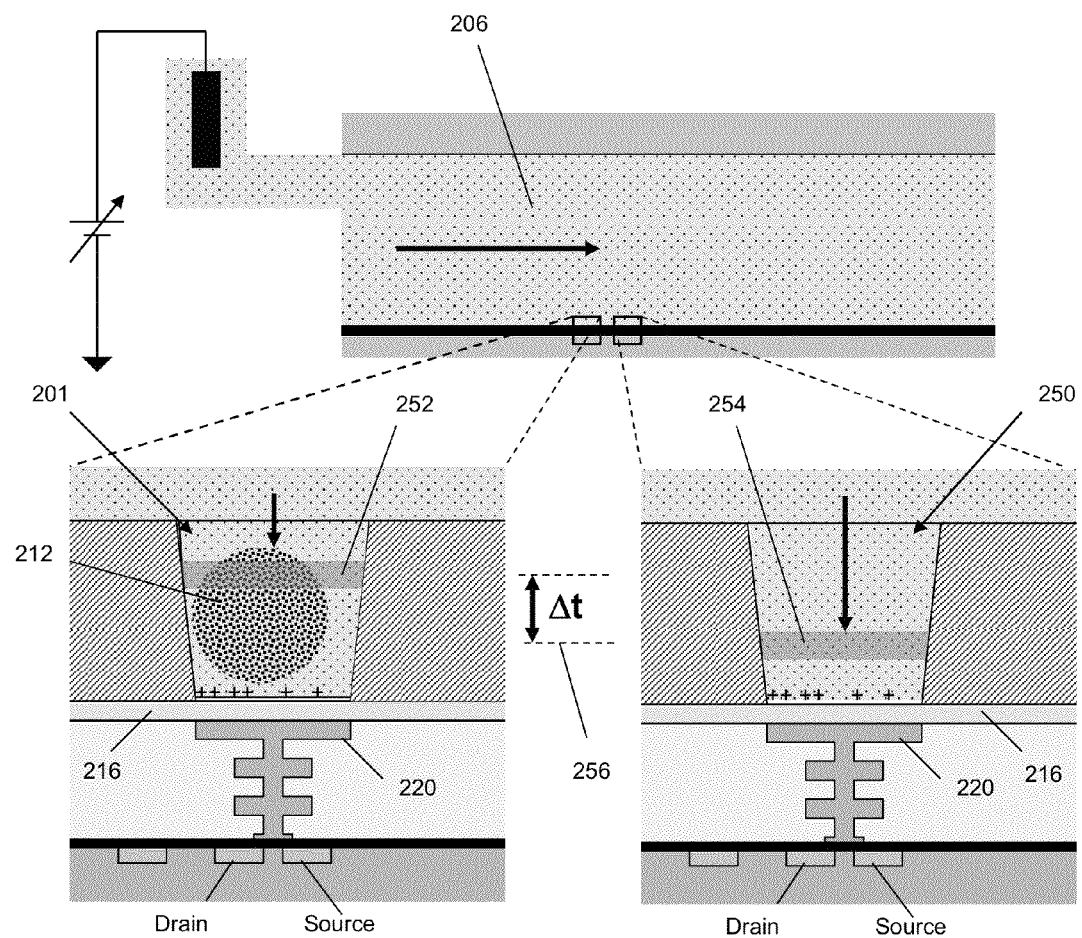
FIG. 2C illustrates how a particle retards the progress of a sensor-active reagent, thereby creating an output signal time delay that may be used to determine the presence of the particle in the microwell.
Figure 2D:
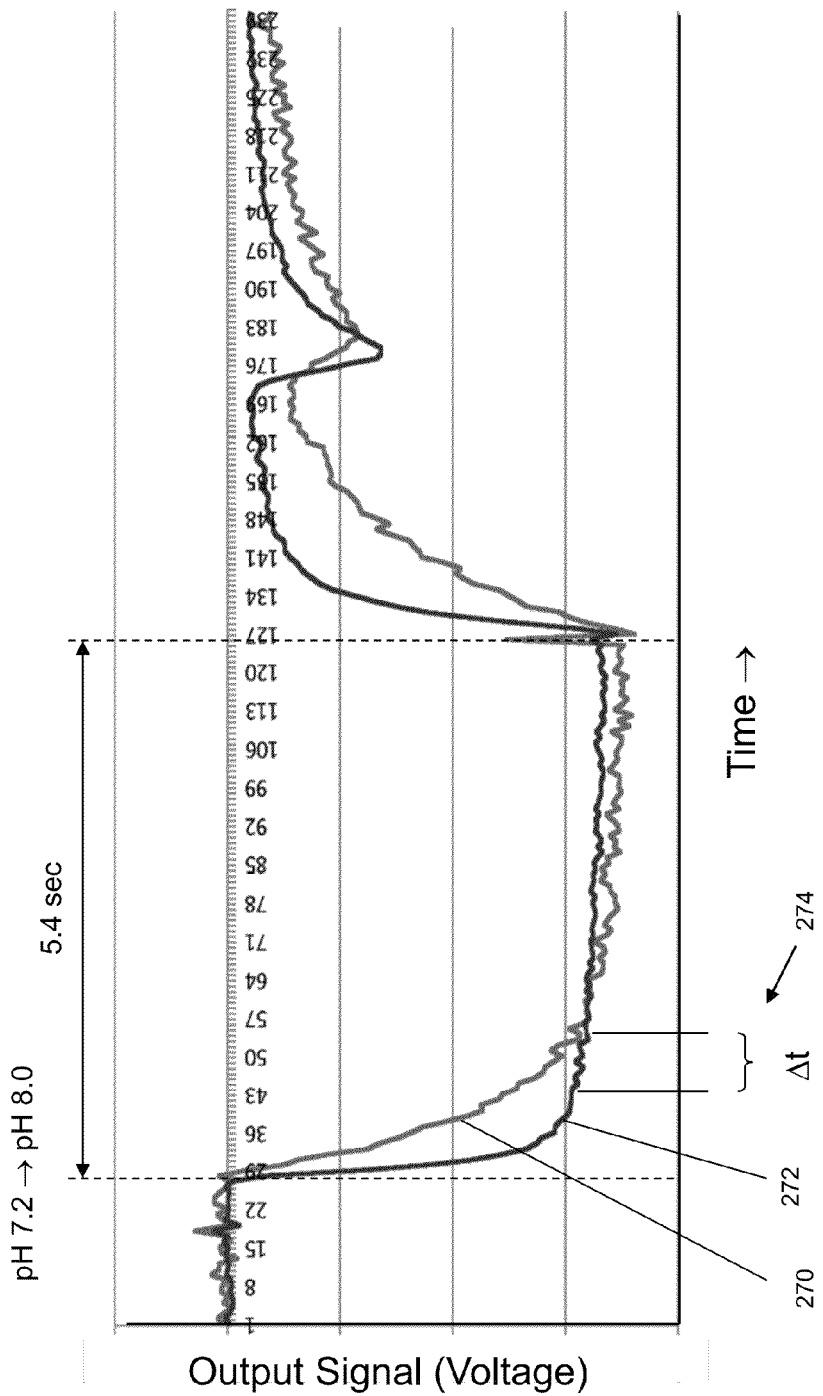
FIG. 2D compares output signal data from a microwell with a particle and a microwell without a particle.
Figure 3B:
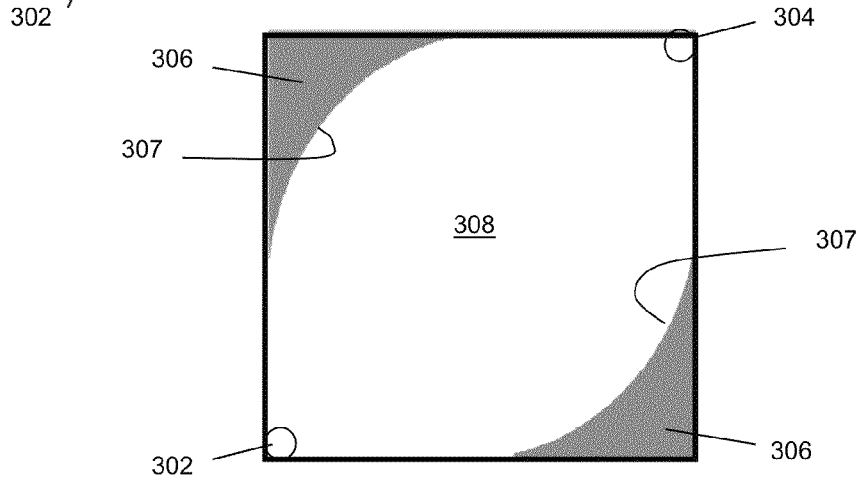
FIG. 3B is a top view of a mask used for fabricating a sensor array of floating gate chemFET, where floating gates of chemFETs outside of a diagonal flow region are electrically connected in the manufacturing process, in order to eliminate or minimize noise contributions from unused sensors outside of the diagonal flow region.
Figure 3C:
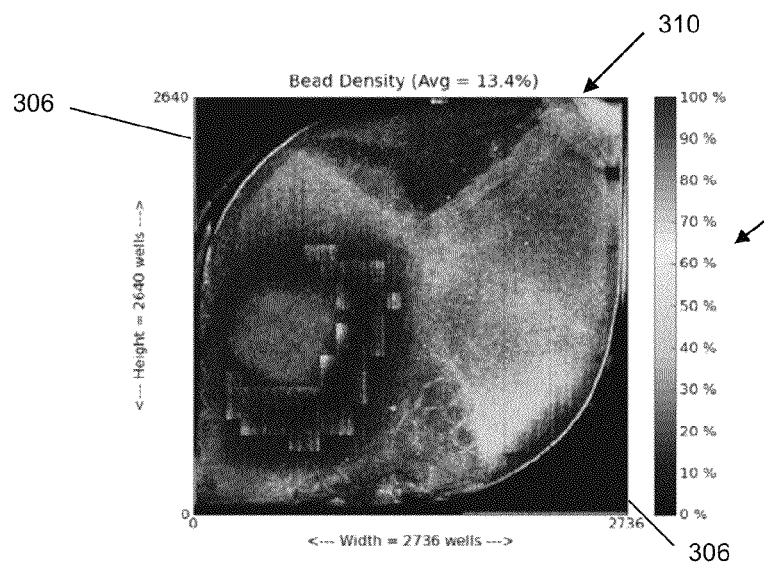
FIG. 3C is a display showing the density of analyte deposition in a large-scale microwell array as determined by sensor output signal changes in response to exposure to a step-function pH change.

As illustrated in FIG. 2C, when sensor-active reagent flows into the flow chamber, it diffuses from flow chamber (206) through microwell (201) that contains particle (212) as well as through microwell (250) and to the region of passivation layer (216) opposite of sensor plate (220). Whenever microwell (201) contains analyte or particle (212), diffusion front (252) of the charging reagent is retarded relative to front (254) in empty well (250) either by the physically obstruction in the diffusion pathway by the analyte/particle or by chemical interactions with the analyte/particle or its associated solid support, if present. Thus, microwells containing analyte may be determined by correlating a time delay (256) in the change of output signal of the sensor with the presence of analyte/particle. In one embodiment, where the sensors are configured to measure pH, the charging reagent is a solution having a predetermined pH, which is used to replace a first reagent at a different predetermined pH. In embodiments for nucleic acid sequencing, the retardation of hydrogen ion diffusion is affected both by the physical obstruction and buffering capacity of the analyte and/or particle. Preferably, the first reagent pH is known and the change of reagents effectively exposes sensors of the microwells to a step-function change in pH, which will produce a rapid change in charge on their respective sensor plates. In one embodiment, a pH change between the first reagent and the charging reagent (or sometimes referred to herein as the "second reagent" or the "sensor-active" reagent) is 2.0 pH units or less; in another embodiment, such change is 1.0 pH unit or less; in another embodiment, such change is 0.5 pH unit or less; in another embodiment, such change is 0.1 pH unit or less. The changes in pH may be made using conventional reagents, e.g. HCl, NaOH, or the like. Exemplary concentrations of such reagents for DNA pH-based sequencing reactions are in the range of from 5 to 200 µM, or from 10 to 100 µM. The variation in charge at a microwell surface opposite a sensor plate indicative of the presence or absence of analyte (or a byproduct from a reaction on an analyte) is measured and registered as a related variation in the output signal of the sensor, e.g. a change in voltage level with time. FIG. 2D shows data from sensors on an array manufactured in accordance with Rothberg et al, U.S. patent publication 2009/0127589, with sensor layout, pitch (9 µm), and floor plan as described in FIGS. 10, 11A, and 19. A microwell corresponding to a first sensor is loaded with a 5.9 µm diameter bead with template, primer and polymerase attached and a microwell corresponding to a second sensor is empty. The output signals from each sensor are recorded while the reagent in a flow cell is changed from pH 7.2 to pH 8.0 and maintained at the pH 8.0 value for 5.4 sec. Curve (270) shows the values of the output signal from the first sensor (whose microwell contains a bead) and curve (272) shows values of the output signal from the second sensor (whose microwell is empty). Both curves show a change from a high value corresponding to pH 7.2 to a low value corresponding to pH 8.0. However, the signal corresponding to the empty well reaches the low value noticeably faster than the signal corresponding to the bead-bearing microwell. The difference in time, $\Delta t$ (274), at which the respective output signals reach the lower value, or a comparable measure, is readily determined with conventional data analysis techniques. Locations and densities of particle-containing microwells within an array may be displayed graphically in a number of ways, including as a contour map or "heat" map, as illustrated in FIG. 3C.

In one aspect of the invention, microwell arrays may be provided with locations of randomly distributed analytes determined. Such a product, or article of manufacture, comprises (i) a sensor array comprising a plurality of sensors formed in a circuit-supporting substrate, each sensor of the array being configured to generate at least one electrical signal related to a concentration or presence of one or more predetermined species proximate thereto and a microwell array disposed on the circuit-supporting substrate such that each microwell thereof has an opening on a surface of the microwell array and is disposed on at least one sensor; and (ii) a plurality of analytes randomly distributed in the microwells at locations determinable by an output signal generated by its corresponding sensor. In one embodiment, the analytes comprise particles having attached thereto clonal populations of DNA fragments, e.g. genomic DNA fragments, cDNA fragments, or the like.

Flow Cells and Output Signal Collection

Flow cell designs of many configurations are possible; thus the system and methods presented herein are not dependent on use of a specific flow cell configuration. Design and performance specifications of a flow cell of the invention include, but are not limited to the following: (i) minimization of the time required to change reagents that analytes are exposed to, (ii) minimization of mixing of successive reagents, that is, providing a uniform flow front between successive reagents, (iii) provide a laminar flow and uniform transit times of fluids across an array (including minimization or elimination of any regions (such as dead volumes) where fluids become trapped so that mixing between successive flows can occur), (iv) provide sufficient volume of flow over microwells (for example, by providing a flow chamber of sufficient volume above the microwell array) so that efficient exchange of material by diffusion occurs between the microwell volumes and the flow), (v) minimization of bubble formation (including reducing sharp corners or edges that promote bubble formation, controlling dissolved gas in the reagents, and providing surfaces that are readily wetted by aqueous reagents), (vi) facilitation of the placement of a reference electrode, (vii) facilitation of loading analytes into microwells or reaction chambers in an array, and the like.

In one aspect, a flow cell of the invention directs reagent flows to a microwells array such that each microwell is exposed to substantially the same flow conditions, including flow rate, concentration, and the like, at substantially the same time throughout the microwell array, as reagents are delivered to the array. By "substantially the same time" in reference to such exposure it is meant that the transit time through the flow chamber of a boundary between two successive reagents is small in comparison to the length of time a microwell is exposed to any one reagent. For some flow cell configurations identical flow rates at each microwell are not possible, such as with flow cells having inlets and outlets located diagonally in a flow chamber constrained to a rectilinear space. Nonetheless, a preferred design feature is that differences in flow conditions, such as flow rate, experienced by different microwells are minimized by a flow chamber and the flow path it defines. As mentioned above, a flow cell can have a variety of designs for achieving the above performance and manufacturing criteria, such as disclosed in Rothberg et al, U.S. patent publication 2009/0127589; Rothberg et al, U.K. patent application GB24611127. A flow cell of the invention that meets such design and performance criteria is illustrated in FIGS. 4A to 4E. The illustrated designs provide for simple manufacture where a flow cell is formed by attaching a component with inlet and outlet to a chip, or encapsulated microwell array-sensor array unit. In this embodiment, a flow chamber is the interior space formed when such pieces are combined, or attached to one another. In the design, an inlet is positioned at a corner of the flow chamber and an outlet at the diagonally opposed corner. This design is simple in that it requires only two manufactured pieces and the diagonal positioning of the inlet and outlet minimizes regions (e.g. (301) in FIG. 3A) of the flow chamber where reagent may be trapped or their transit times retarded. FIG. 3A illustrates flow paths (300) of a reagent as it transits a flow chamber along its diagonal axis from inlet (302) to outlet (304). In one embodiment, a flow chamber is defined by reference to such flow paths, as shown in FIG. 3B. That is, in the example of FIG. 4A, walls (410) and the boundary (307) (defining "pinned" sensors, described more fully below) are shaped to substantially follow the flow paths that reagents would follow through a square or rectangular flow chamber with diagonally opposed inlet and outlet. The result is that reagent flows are confined to central region (308) and corner regions (306), where reagents could mix or form eddies, are rendered inaccessible. The curvature of boundary (307) may be estimated (for example using a section of a quadratic or like standard curve) or it may be computed using commercially available fluid dynamics software, e.g., SolidWorks from Dassault Systems (Concord, Mass.); Flowmaster from FlowMaster USA, Inc. (Glenview, Ill.); and OpenFOAM (open source code for computational fluid dynamics available on the world wide web, www.openefd.co.uk). In embodiments employing floating gate chemFETs as sensors, preferably, sensors in the reagent-inaccessible regions (306) are electrically connected so as not to introduce spurious voltage levels into output signals generated in those sections of the sensor array. That is, in such embodiments, readout circuitry of the sensor array continues to readout all columns and all rows, so that specialized circuits or programming is not required to avoid the sensors in the inaccessible regions. Instead, constant predetermined output signals are registered from sensors in such regions.

In one aspect of the invention described above, reaction chambers or microwells containing analytes are identified by introducing successive reagents (referred to herein as a first reagent and a predetermined reagent) into the flow cell that change the charge sensed by the sensors of the array in a predetermined manner. As shown in FIG. 3C, results of such identification may be displayed as a density map of the microwell array (310) in the flow chamber, where the distribution of analytes within microwells of the array are indicated by color scale (312). In this embodiment, colors of scale (312) indicate a local percentage of microwells (e.g. percentage of each non-overlapping regions of 100 microwells) containing analytes throughout the array, except for unused regions (306).

Figure 4A:
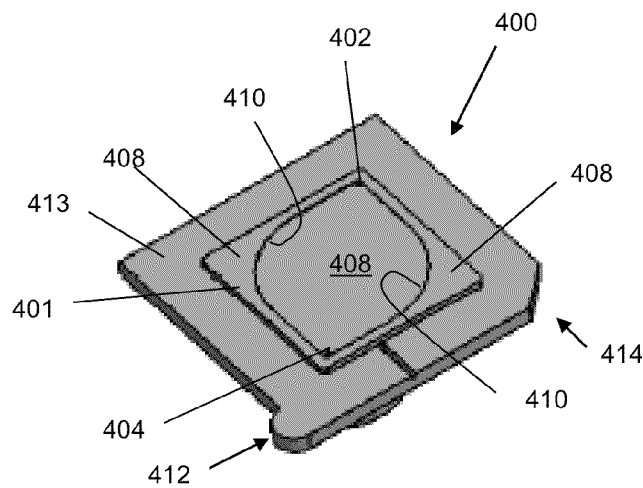
FIG. 4A-4D show different views of flow cell components and their integration with a microwell-sensor array chip.
Figure 4B:
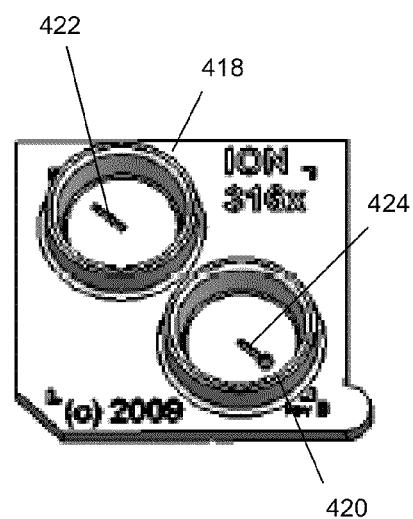
Figure 4C:
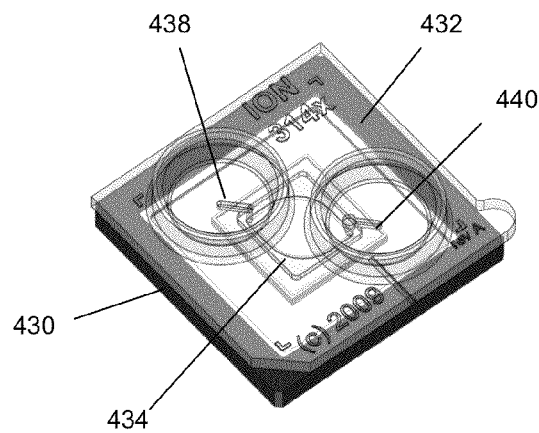
Figure 4D:
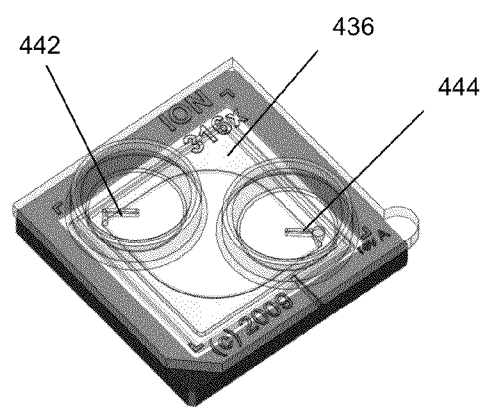

Flow cells may be assembled with a microwell array and sensor array in a variety of ways, such as disclosed in Rothberg et al, U.S. patent publication 2009/0127589 and Rothberg et al, U.K. patent application GR24611127, which are incorporated by reference. In one embodiment, illustrated in FIGS. 4A-4D, a flow cell is made by attaching a fluidic interface member to a housing containing a sensor chip. Typically, an integrated microwell-sensor array (i.e., a sensor chip) is mounted in a housing or package that protects the chip and provides electrical contacts for communicating with other devices. A fluidics interface member is designed to provide a cavity or flow chamber for reagents to pass through when it is sealingly attached to such packaging. In one aspect, such attachment is accomplished by gluing the pieces together. FIG. 4A shows a bottom view (or face) of component (400) (referred to below as a "rectilinear body") of a flow cell of the invention. In the illustrated embodiment, a complete flow cell is formed by attaching component (400) to a package containing a sensor array (as shown in FIGS. 4C and 4D). Ridge (401) is elevated from surface (413) and forms walls (410) of ellipsoidal flow chamber (408) when mated with chip (430) shown in FIG. 4C. Component (400) may be glued to chip housing (430) (referred to below generically as "rectilinear interface package") to form a fluid-tight seal. FIG. 4B shows a top view (or face) (416) of component or member (400) showing inlet and outlet collars (418) and (420) that permit the flow cell to be sealingly connected to a fluidic system. Inlet and outlet tubes connected to elastomeric annular members that are inserted into collars (418) and (420) so that the elastomeric material forms a seal along the floor and walls of collars (418) and (420). Other means of connecting a flow cell to a fluidics system may be used, including other types of pressure fittings, clamp-based fittings, screw-on fittings, or the like, which are design choices for one of ordinary skill. Component (400) may be adapted to accommodate different sized chips with a simple design change, as illustrated by passages (422) and (424). Namely, for a small array (434) shown in FIG. 4C, a passage having an opening at the center of inlet collar (418) and of outlet collar (420) may be directed by such passage towards the center of component or member (400) to an inlet port and outlet port over array (430). Likewise, for a large array (436), shown in FIG. 4D, similar passages (442 and 444) may be directed away from the center of component (400) and to the inlet and outlet of array (436). This has the advantage of providing a single basic flow cell design that can be used with multiple sensor array sizes. Protruding tab (412) and bevel (414) are employed to ensure correctly oriented placement of a chip into a complementary socket or appliance for making fluidic and electrical connections to the rest of the apparatus.

In one aspect, the invention includes a flow cell member (exemplified in FIGS. 4A and 4B) for forming a fluidics interface with sensor arrays of different rectilinear sizes disposed in a rectilinear interface package. Such a member comprises the following elements: (a) a rectilinear body having an upper face and a lower face and a shape matched with that of the rectilinear interface package so that the lower face of the rectilinear body may be bonded to the rectilinear interface package to form a fluid-tight enclosure for a sensor array, wherein an inlet is disposed at one end of the upper face, and an outlet is disposed at an opposite end of the upper face; (b) an inlet passage interior to the rectilinear body providing a fluid passage from the inlet to the fluid-tight enclosure forming an inlet port in the lower face of the rectilinear body positioned above and at one end of the sensor array: and (c) an outlet passage interior to the rectilinear body providing a fluid passage from the outlet to the fluid-tight enclosure forming an outlet port in the lower face of the rectilinear body positioned above and at an end of the sensor array opposite of that of the inlet port. In one embodiment, the inlet is concentrically disposed with an inlet collar in a corner of said upper face and said outlet is concentrically disposed with an outlet collar in a diagonally opposite corner of said upper face as said inlet and inlet collar. In another embodiment, the inlet and outlet collars each have a radius and wherein said inlet port and said outlet port are each positioned within perpendicular projections of the radii of said inlet and outlet collars, respectively, onto said lower face of said rectilinear body. In another embodiment, a plurality of fluid-tight enclosures are formed when a rectilinear body is bonded to a rectilinear interface package, as exemplified in FIG. 4E.

Figure 4E:
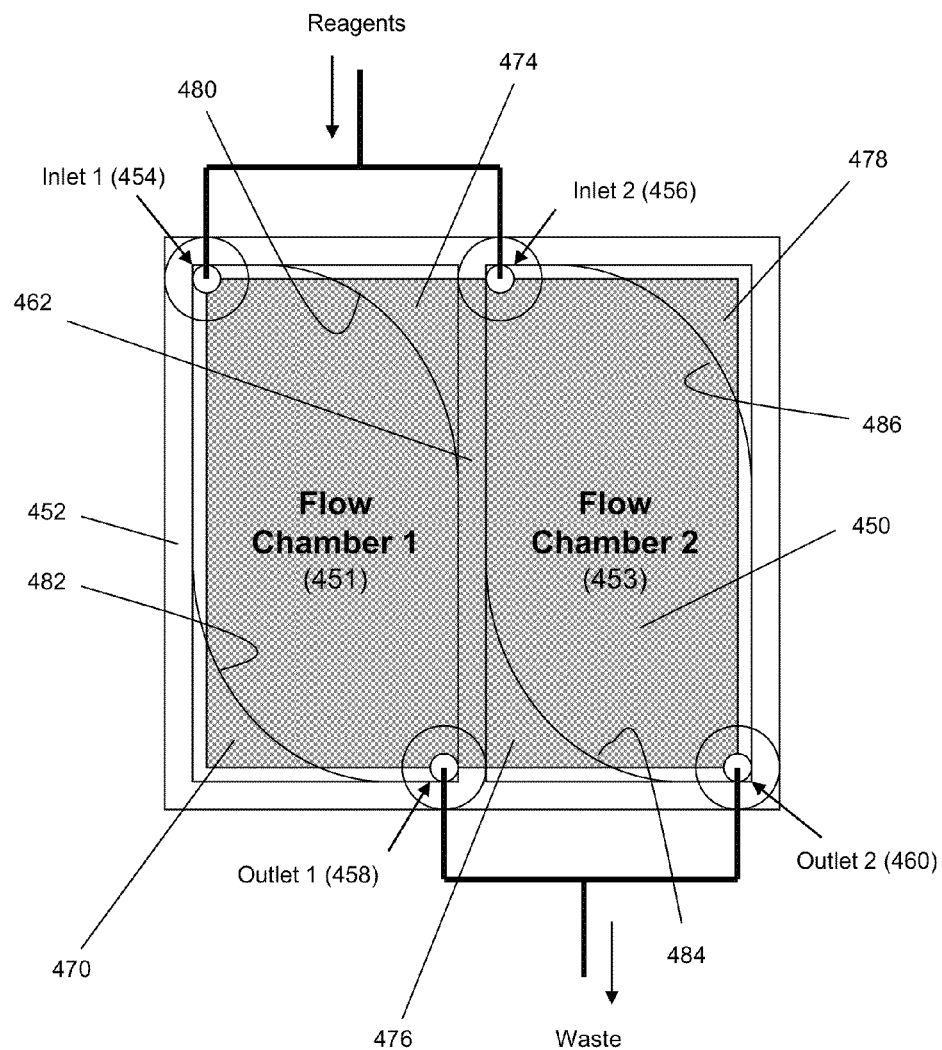
FIG. 4E shows a flow cell with two flow chambers integrated with a microwell-sensor chip.

FIG. 4E illustrates how the above design concepts may be used to make a plurality of separate flow cells using a single large sensor array. Fluidics interface member (462) mounts on and is sealingly attached to a housing (not shown) that holds sensor array (450) and defines two flow chambers (451) and (453), each having separate inlets (454 and 456, respectively) and separate diagonally opposed outlets (458 and 460, respectively) that are connected to a common source of reagents and to a common waste line, respectively. Interior walls (480, 482, 484 and 486) formed by attachment of fluidics interface member (452) to the chip housing defines the flow paths through flow chambers (451) and (453) and exclude opposing corner regions (470, 474, 476, and 478) from having contact with reagents passing through the flow chambers. Preferably, in embodiments employing floating gate FETs, sensors in corner regions (470, 474, 476, and 478) are pinned as described above. Likewise, sensors in the region defined by, or under, central partition (462) are also pinned so that they do not contribute to output signal noise of active sensors.

Flow cells and fluidic circuits of the invention (described below) may be fabricated by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For small scale fluid deliveries, microfluidic fabrication techniques are well-suited for making fluidics circuits of the invention, and guidance for such techniques is readily available to one of ordinary skill in the art, e.g. Malloy, Plastic Part Design for Injection Molding: An Introduction (Hanser Gardner Publications, 1994); Herold et al, Editors, Lab-on-a-Chip Technology (Vol. 1): Fabrication and Microfluidics (Caister Academic Press, 2009); and the like. For meso-scale and larger scale fluid deliveries, conventional machining techniques may be used to fabricate parts that may be assembled into flow cells or fluidic circuits of the invention. In one aspect, plastics such as polycarbonate, polymethyl methacrylate, and the like, may be used to fabricate flow cells and fluidics circuits of the invention.

Figure 5A:
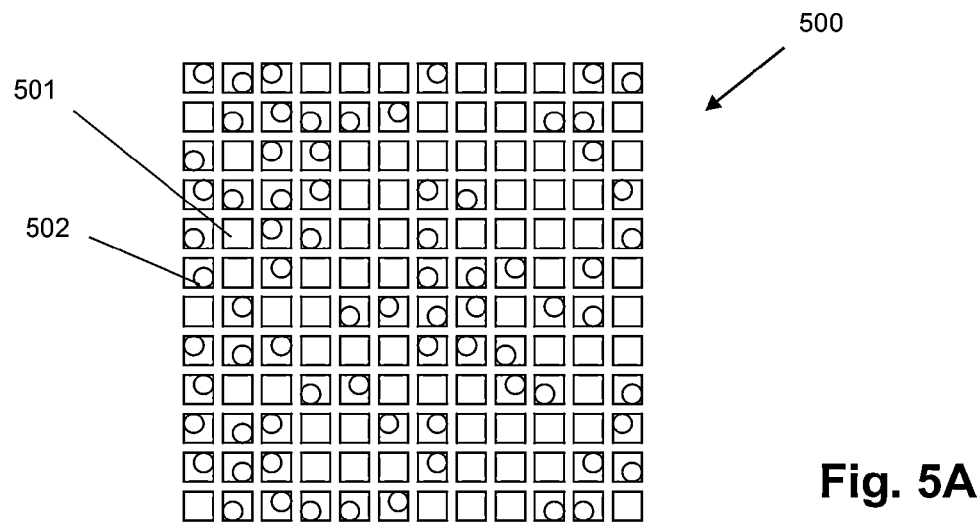
FIG. 5A illustrates analytes randomly disposed in microwells of a microwell array.
Figure 5B:
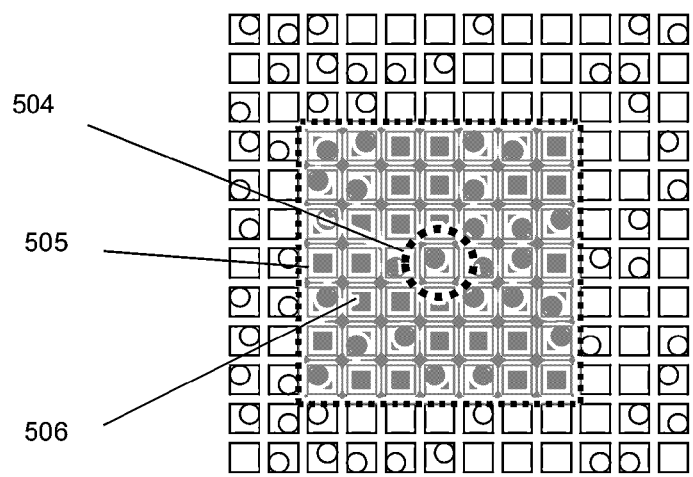
FIGS. 5B and 5C illustrate different ways of identifying empty microwells in the vicinity of a selected microwell.
Figure 5C:
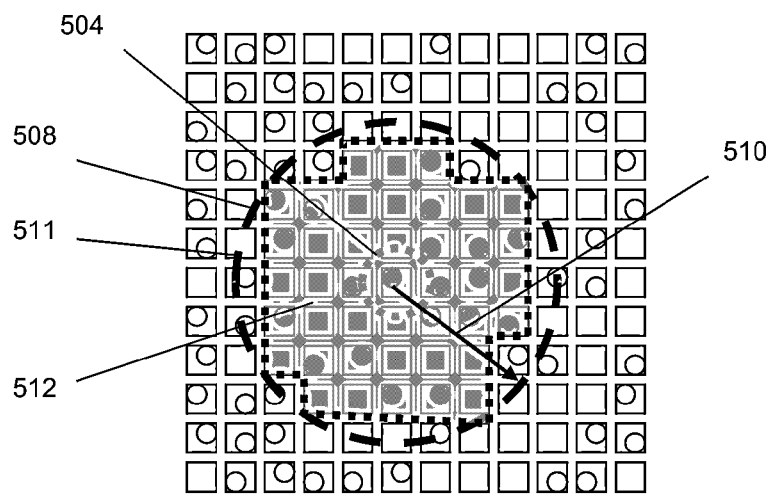

As mentioned above, analytes are randomly distributed in microwells of an array, as illustrated for array section (500) in FIG. 5A, where microwells either are empty (501) or contain analyte (502), such as a bead. Output signals collected from empty wells may be used to reduce or subtract noise in output signals collected from sensors of microwells containing analyte. Empty well output signals contain signal noise components common to all microwells within a local region of the array, so that such common noise components may be obtained from the empty well output signals and subtracted from the output signal of microwells with analyte using conventional signal processing techniques. In other words, output signals from wells containing analyte are improved by subtracting a component of noise determined from output signals of neighboring empty wells. In one aspect, a measure of such common noise is based on an average of output signals from multiple neighboring empty wells. As described more fully below in the case of DNA sequencing, the type of information used from neighboring microwells and how it is used may vary with nature of assays being carried out and measured. As used herein, the term "average" includes weighted averages, and functions of averages, for example, based on models of physical and chemical processes taking place in the microwells. Types of microwells used in the averages may be generalized in particular applications where, for example, further sets of microwells may be analyzed for further information on common noise, such as, in addition to empty wells, wells containing particles without analyte may be included, and so on. In one embodiment, time domain functions of average empty well noise may be converted to frequency domain representations and Fourier analysis, e.g. using fast Fourier transforms, may be used to remove common noise components from output signals from non-empty well. As mentioned above, the empty well signal subtracted in this manner may be an average of empty well signals of empty wells in the vicinity of a microwell of interest. The number and location of local empty wells for such computation may be selected and carried out in a variety of ways. Exemplary approaches for making such selections are illustrated in FIGS. 5B and 5C. In FIG. 5B, for each microwell containing analyte (504), a fixed region (506) may be defined by a 7×7 square (505) of microwells. In other embodiments, such a fixed region may vary in the range from 3×3 to 101×101, or in the range from 3×3 to 25×25. Selection of the size of such regions depend several factors, including the degree of loading of analytes in microwells, the amount of time available for computing during a step, and the like. Returning to FIG. 5B, output signals from empty wells in region (506) are used in the above subtraction computation. Alternatively, a region of empty wells may be determined by distance from the microwell of interest, as illustrated in FIG. 5C. There fixed circular region (512) is defined by a distance (510) from the microwell of interest (504) and empty well signals from empty wells falling entirely within region (512), that is, in region (508), are used in the above subtraction computation. Not all of the empty well signals in a given region need be used. For example, when a microwell array is sparsely loaded with analytes or particles, e.g. less than 25 percent microwells being loaded, a portion of the empty wells in a defined region (e.g. 512) may be used for background subtraction. In one aspect, such portion or subset may be a randomly selected subset of available empty wells. In some circumstances it may be advantageous to use the least number of empty well output signals as possible in order to minimize computation time for determining output signals from non-empty wells. The area and/or number of wells selected for determining an average empty well signal may change according to the density of analytes in microwells. For example, the size of a local region may be selected depending on the availability of empty wells. If a minimum of N empty well output signals, e.g. 10, 20, or 30, must be measured to ensure a reliable representation of local noise, then a local region, e.g. (512), may be increased until such number is present. In one aspect, local noise subtraction using a fixed area is used whenever ninety-five percent or less of the microwells in an array contain analyte. In some embodiments, in addition to, or in lieu of empty wells, particles carrying analyte may be spiked with particles not carrying analyte and the background noise subtraction may be with respect to an average signal recorded for microwells containing analyte-free particles.

System for Nucleic Acid Sequencing

Figure 6A:
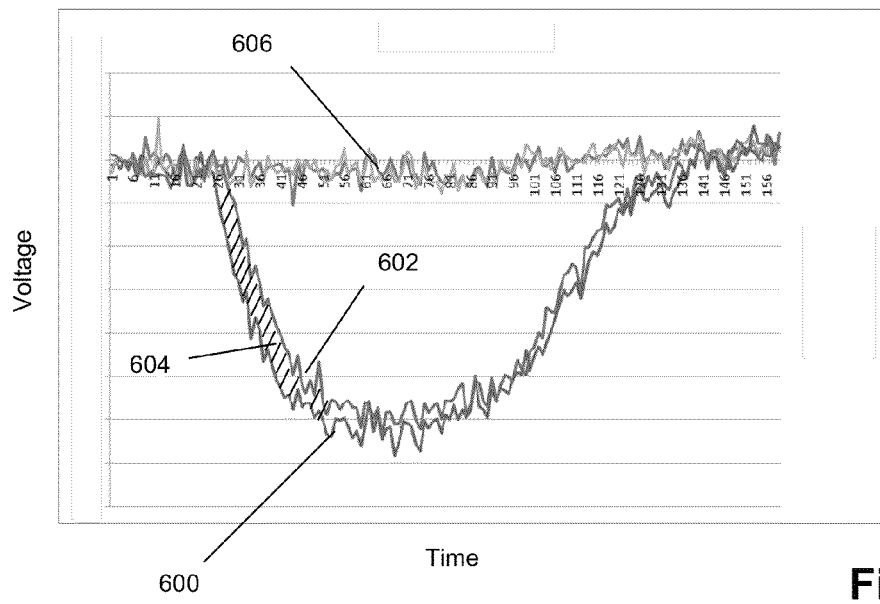
FIGS. 6A-6F illustrate the use of signals from local microwells to reduce noise in an output signal of a sensor of a selected microwell.
Figure 6B:
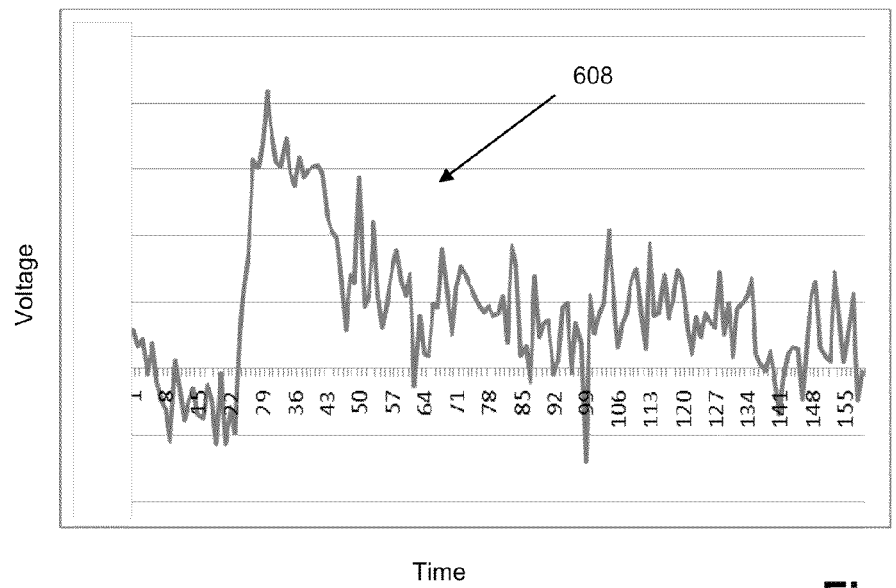
Figure 6C:
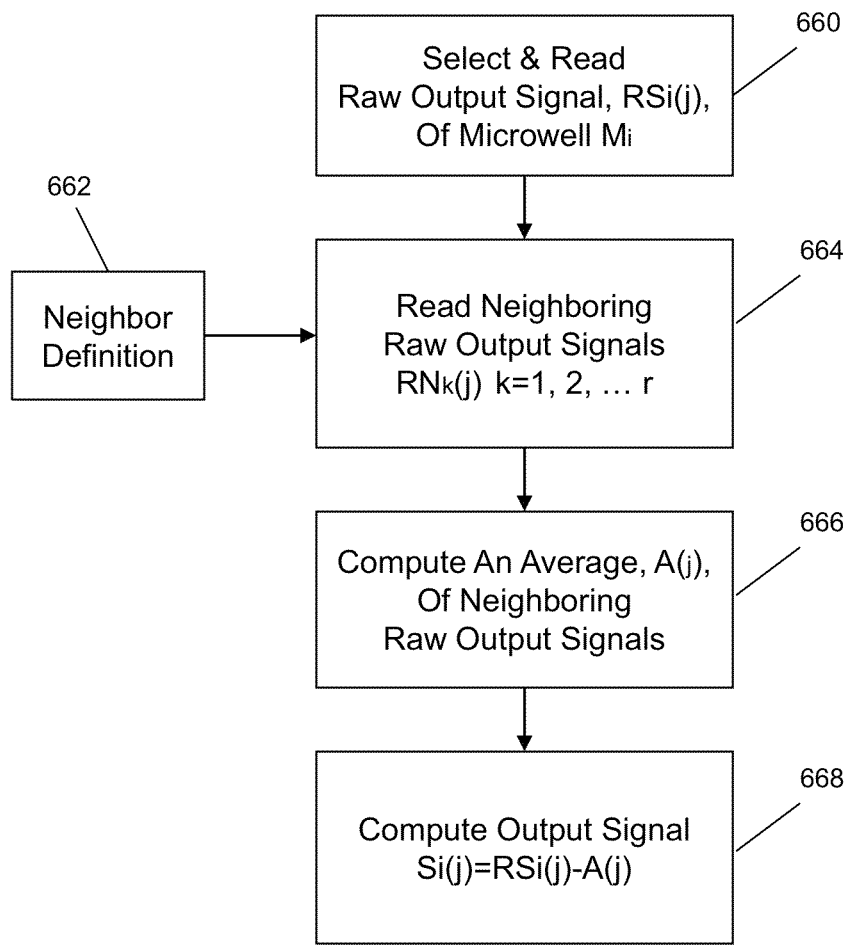
Figure 6D:
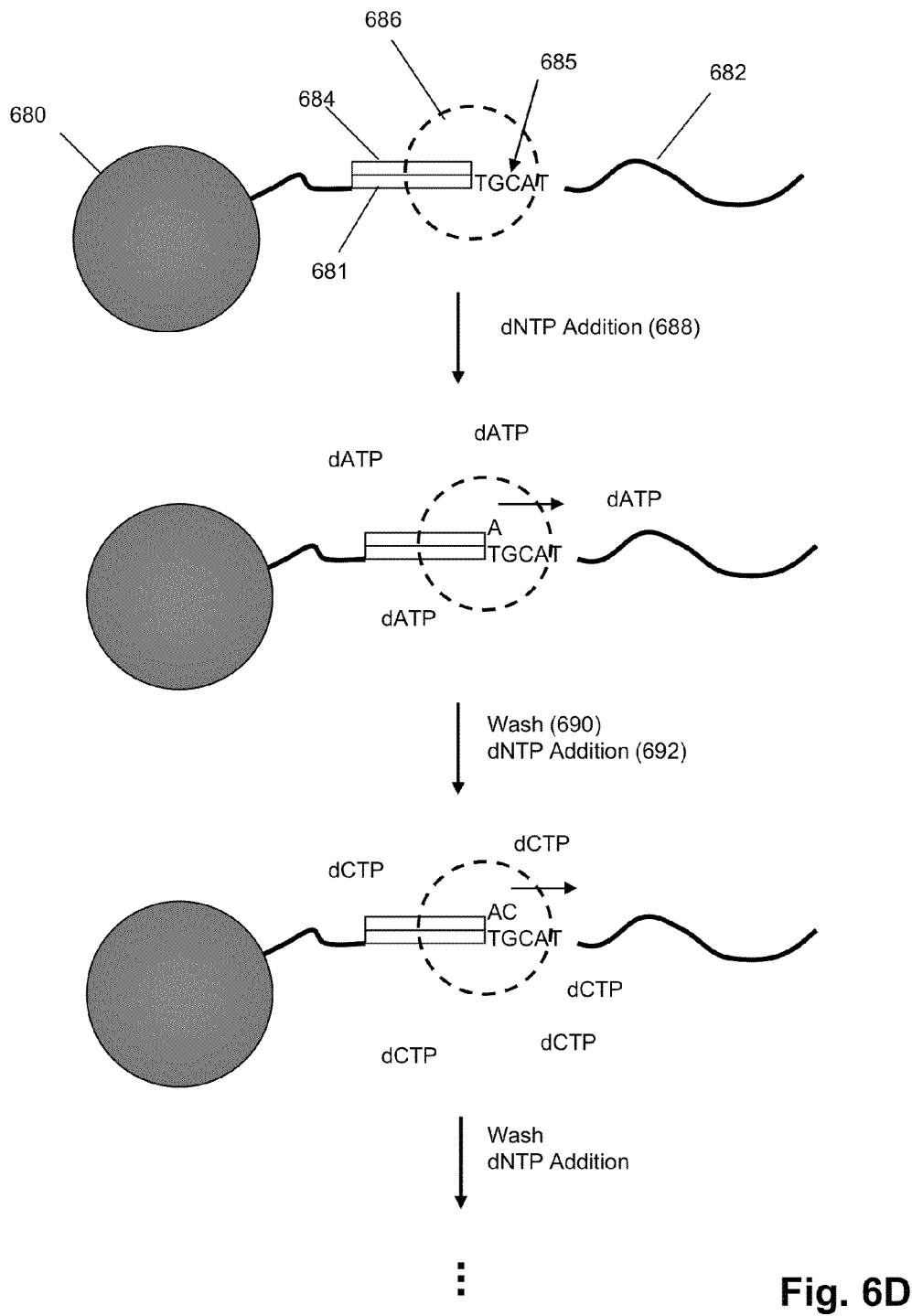

In one aspect, the invention provides methods and apparatus for carrying out label-free DNA sequencing, and in particular, pH-based DNA sequencing. The concept of label-free DNA sequencing, including pH-based DNA sequencing, has been described in the literature, including the following references that are incorporated by reference: Rothberg et al, U.S. patent publication 2009/0026082; Anderson et al, Sensors and Actuators B Chem., 129: 79-86 (2008); Pourmand et al, Proc. Natl. Acad. Sci., 103: 6466-6470 (2006); and the like. Briefly, in pH-based DNA sequencing, base incorporations are determined by measuring hydrogen ions that are generated as natural byproducts of polymerase-catalyzed extension reactions. In one embodiment, templates each having a primer and polymerase operably bound are loaded into reaction chambers (such as the microwells disclosed in Rothberg et al, cited above), after which repeated cycles of deoxynucleoside triphosphate (dNTP) addition and washing are carried out. In some embodiments, such templates may be attached as clonal populations to a solid support, such as a microparticle, bead, or the like, and such clonal populations are loaded into reaction chambers. For example, templates may be prepared as disclosed in U.S. Pat. No. 7,323,305, which is incorporated by reference. As used herein, "operably bound" means that a primer is annealed to a template so that the primer's 3' end may be extended by a polymerase and that a polymerase is bound to such primer-template duplex, or in close proximity thereof so that binding and/or extension takes place whenever dNTPs are added. In each addition step of the cycle, the polymerase extends the primer by incorporating added dNTP only if the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there is a number of contiguous identical complementary bases in the template (i.e. a homopolymer region), the number of hydrogen ions generated, and therefore the magnitude of the local pH change, is proportional to the number of contiguous identical complementary bases. (The corresponding output signals are sometimes referred to as "1-mer", "2-mer", "3-mer" output signals, and so on). If the next base in the template is not complementary to the added dNTP, then no incorporation occurs and no hydrogen ion is released (in which case, the output signal is sometimes referred to as a "0-mer" output signal.) In each wash step of the cycle, an unbuffered wash solution at a predetermined pH is used to remove the dNTP of the previous step in order to prevent misincorporations in later cycles. Usually, the four different kinds of dNTP are added sequentially to the reaction chambers, so that each reaction is exposed to the four different dNTPs one at a time, such as in the following sequence: dATP, dCTP, dGTP, dTTP, dATP, dCTP, dGTP, dTTP, and so on, with each exposure followed by a wash step. The process is illustrated in FIG. 6D for template (682) with primer binding site (681) attached to solid phase support (680). Primer (684) and DNA polymerase (686) operably bound to template (682). Upon the addition (688) of dNTP (shown as dATP), polymerase (686) incorporates a nucleotide since "T" is the next nucleotide in template (682). Wash step (690) follows, after which the next dNTP (dCTP) is added (692). Optionally, after each step of adding a dNTP, an additional step may be performed wherein the reaction chambers are treated with a dNTP-destroying agent, such as apyrase, to eliminate any residual dNTPs remaining in the chamber, which may result in spurious extensions in subsequent cycles.

In one embodiment, a sequencing method exemplified in FIG. 6D may be carry out using the apparatus of the invention in the following steps: (a) disposing a plurality of template nucleic acids into a plurality of reaction chambers disposed on a sensor array, the sensor array comprising a plurality of sensors and each reaction chamber being disposed on and in a sensing relationship with at least one sensor configured to provide at least one output signal representing a sequencing reaction byproduct proximate thereto, and wherein each of the template nucleic acids is hybridized to a sequencing primer and is bound to a polymerase; (b) introducing a known nucleotide triphosphate into the reaction chambers; (c) detecting incorporation at a 3' end of the sequencing primer of one or more nucleotide triphosphates by a sequencing reaction byproduct if such one or more nucleotide triphosphate are complementary to corresponding nucleotides in the template nucleic acid; (d) washing unincorporated nucleotide triphosphates from the reaction chambers; and (e) repeating steps (b) through (d) until the plurality of template nucleic acids are sequenced. For embodiments where hydrogen ion is measured as a reaction byproduct, the reactions further should be conducted under weak buffer conditions, so that the maximum number of hydrogen ions reacts with a sensor and not extraneous components (e.g. microwell or solid supports that may have surface buffering capacity) or chemical constituents (in particular pH buffering compounds). In one embodiment, a weak buffer allows detection of a pH change of at least ±0.1 in said reaction chamber, or at least ±0.01 in said reaction chambers.

Several potential sources of noise may affect output signals from sensors when a large number of electrochemical reactions are carried out in a microwell array integrated with a sensor array, such as described by Rothberg et al (cited above). Such sources of noise include thermal sensitivity of the sensors, electrical potential disturbances in the fluid (such as resistive or thermal noise in the fluids, reference voltage changes due to different fluids contacting the reference electrode, and the like) and pH changes due to bulk changes in fluids that are passed over the sensor array (referred to herein as "reagent change noise"). Additional sources of noise may also arise in DNA sequencing applications from the nature of a particular DNA sequencing chemistry employed. For example, noise may arise due to the stochastic behavior of polymerase function (incomplete extensions) or failure to completely wash away all dNTPs in a given step (inappropriate incorporation), e.g. Chen et al, International patent publication WO/2007/098049.

Thermal sensitivity of a sensor array is addressed by maintaining the sensor array at a predetermined temperature that is suitable for extension reactions and that permits measurement of hydrogen ion concentrations and/or changes in the pH. In one aspect, such temperature is within the range of from 25° C. to 75° C. Preferably the predetermined temperature is constant throughout the entire multistep reaction. Such temperature may be regulated by conventional techniques, e.g. Peltier device, or the like. In one embodiment, temperature is maintained by controlling the temperature of the reagents that flow through the flow cell, such that the rate of flow and heat capacity of the fluid is sufficient to remove excess heat generated by the sensors or analytical reactions.

As mentioned above, disturbances in the reference voltage arise from a variety of sources, including changes in the type of fluid a reference electrode is in contact with, and noise from other components of the fluidics system. For example, other components of the fluidics system may act as antennas for extraneous electrical noise, e.g. 60 Hz noise, noise from power supplies, and the like, which affect the reference voltage. In accordance with the invention, a reference electrode is provided that contacts only one kind of reagent throughout a sequencing operation, thereby eliminating a component of reference voltage variability. In another aspect, low frequency noise introduced into the fluidics system may be reduced or eliminated by capacitively coupling the reference electrodes to other components of the fluidics system, such sections of reagent passages in the fluidic systems, as illustrated in FIGS. 7B and 7C.

Another source of noise may arise when successive reagent flows pass over a sensor array (i.e., reagent change noise). The magnitude of such noise depends on several factors including the nature of the measurement being made (e.g. pH, inorganic pyrophosphate (PPi), other ions, or the like) whether a leading or trailing reagent in a reagent change has a property or constituent, e.g. pH, which affects sensor performance and the magnitude of the influence, the relative magnitude of the reagent change effect in comparison with the reaction signal being monitored, and so on. For pH-based DNA sequencing applications (for example), pH-sensitive sensors may generate a signal in response to a reagent change in that is large in comparison to the signal due to hydrogen ion byproduct, as illustrated by the data of FIG. 6A. In such applications, different reagents, such as solutions containing different dNTPs, have slightly different buffering capacities and pKa's, so that at a boundary of different reagent flows. e.g. a wash solution flow followed by a dNTP flow, the sensors register a significant voltage change, as illustrated in FIGS. 2D and 6A. FIG. 6A shows the magnitudes of four output signals from different microwells of a DNA sequencing chip as disclosed is Rothberg et al (cited above), which employs conventional ion-sensitive field-effect transistor (ISFET) sensors. Curves (606) illustrate signals from microwells during a wash step with no changes in reagent. Curve (600) shows an output signal from a microwell containing a particle with template attached where a primer on the template has been extended by one nucleotide. Curve (602) is the output signal from a microwell that contains a particle with a template where there has been no extension. Region (604) is the difference between the two output signals ((602) and (604)) that is due to generation of hydrogen ion in the microwell where extension has taken place. Curve (608) in FIG. 6B, which is the difference between the values of curves (600) and (602), is the part of the raw output signal of curve (600) which is due to hydrogen ion produced in the extension reaction, i.e. the signal of interest. In accordance with the invention, such reagent change noise and other noise components common to local groups of microwells may be subtracted from an output signal of a selected sensor by using information from output signals generated from neighboring microwells. In one embodiment, such neighboring microwell information is obtained from at least one average value of output signals from a plurality of neighboring wells. In another embodiment, neighboring microwell information is obtained from output signals of empty wells. In still another embodiment. neighboring microwell information is obtained from output signals of non-empty microwells where no extension reaction took place. Correction of raw output signals by subtracting reagent change noise may be carried out after each reagent change based on averages computed after each such change, or such corrections may be carried out using averages computed from a previous reagent change, depending on the rate at which averages change during a multi-step or multi-cycle electrochemical process. For example, in a DNA sequencing embodiment, an average may be computed for each different dNTP flow in a cycle (where a succession of the four different dNTPs is introduced into reaction chambers) and used to correct raw output signals for from 1 to 5 cycles of reagent change.

As is noted from FIG. 2D, output signals from neighboring microwells may be systematically altered relative to signals from a microwell of interest depending on the type of neighboring microwells selected for noise subtraction. For example, in FIG. 2D, the same phenomena (e.g., signal delay) that permits the detection of empty wells, may also require that such signals must be transformed to account for such differences if subtraction from the signal of interest is going to make sense. For example, because the presence of a particle in the microwell of interest distorts the signal corresponding to reagent change (delay and flattening due to chemical interaction with the particle), an empty well signal must be modified to remove the changes due to the absence of a particle and chemical interactions, which may readily be done using conventional numerical analysis. If neighboring microwell information is restricted to only 0-mer neighbors, then such transformation is much less, or not necessary, in order to subtract reagent change noise from a signal of interest. As mentioned above, "an average" of neighboring microwell output signals may include weighted averages or transforms of the neighboring microwells' average output signals to reflect the different physical and chemical conditions of the selected microwell and its neighbors. Steps of an embodiment of such a process are illustrated in FIG. 6C. Raw output signal, $RS_i(j)$, for times $j=1, 2 \ldots t$, recorded by a sensor of selected microwell, $M_i$, is read (660). "Raw output signal" means the recorded values of the output signal prior to data analysis. Neighboring microwells are defined (662) so that raw output signals of neighboring microwells, $RN_k(j)$, can also be read (664). Definitions of neighbors may include a local region from where neighbor signals are collected, for example, as described for FIGS. 5A-5C, and such definitions may include the types of neighboring microwells whose output signals are taken, e.g. empty wells, microwells with analyte or particle but no reaction, and the like. In one aspect, neighboring output signals are selected from neighboring microwells that are as physically and chemically similar to the Mi microwell, except for the presence of a signal, e.g. pH level, from the analyte that is to be detected or measured. After raw output signals from neighboring microwells are read, an average, $A(j)$, is computed (666) and subtracted (668) from raw output signal, $RSi(j)$, to give a noise-reduced output signal, $Si(j)$.

Figure 6E:
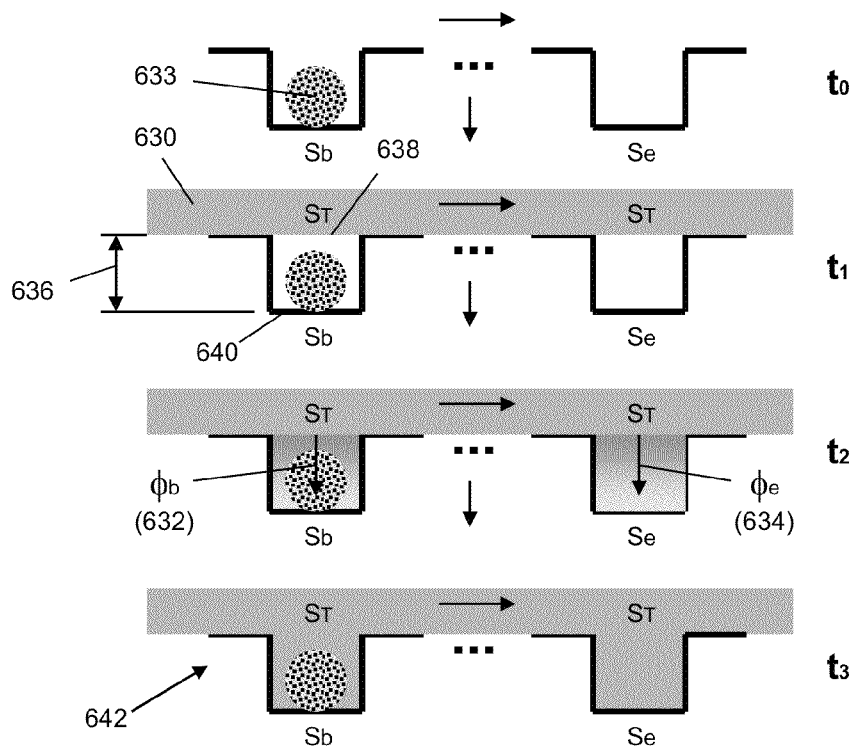
Figure 6F:
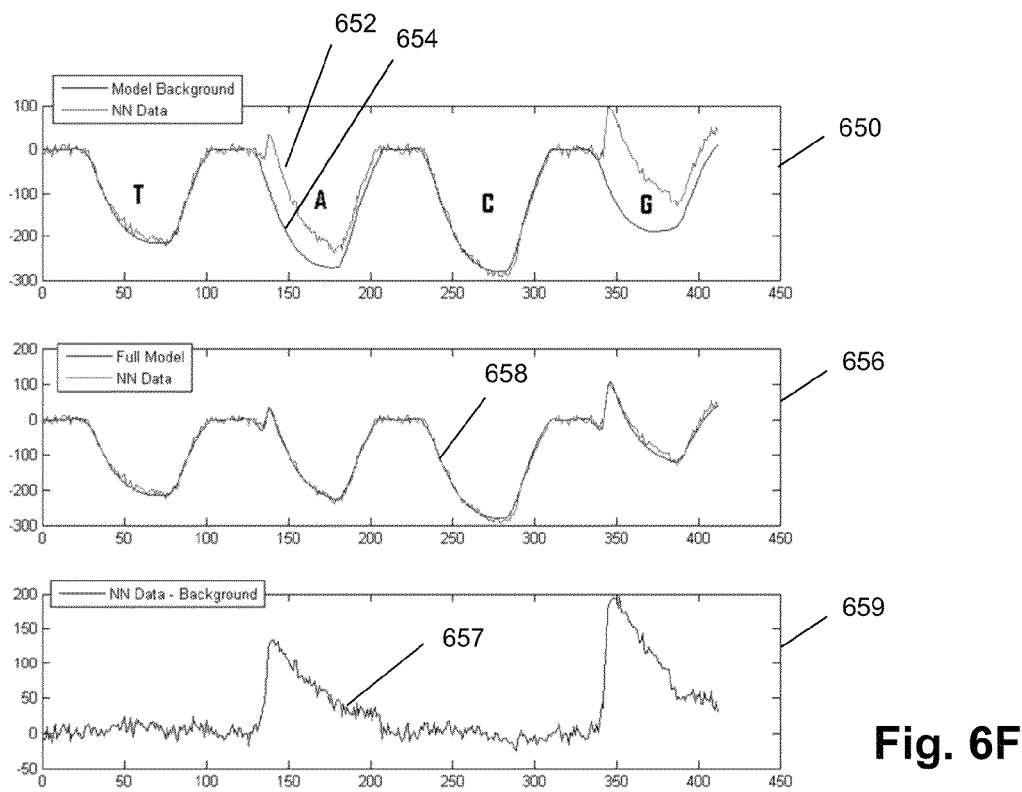

FIG. 6E illustrates another embodiment that uses an average neighbor signal to remove noise from a signal of interest (e.g. change in pH due to nucleotide incorporation). The figure shows two neighboring microwells (631) and (641) at four different times: before a next reagent is introduced ($t_0$), immediately after the next reagent is exposed to the microwells ($t_1$), a time during equilibration of the next reagent with the microwell contents ($t_2$), and after equilibrium has been achieved ($t_3$). The change in sensor signal due to such a reagent change is described as a two compartment model, where one compartment is the next reagent (e.g. the next flow of dNTPs) in region (638) adjacent to the opening of a microwell and the other compartment is the surface (640) at the bottom of a microwell adjacent to the sensor. Immediately after new reagent (630) enters a flow cell a concentration difference (636) is created between the two compartments, so that a flux of hydrogen ions is established both in microwells with particles $\phi_b$ (632) and in empty wells $\phi_e$ (634). For microwells having particles (633) where extension reactions occur, hydrogen ions are also created, which adds to the flux. Eventually equilibrium is reached (642) and the flux of hydrogen ions goes to zero. One of ordinary skill in the art would recognize that a variety of alternative models and models of differing complexity are available for describing the physical and chemical phenomena of the electrochemical reactions taking place in the microwells. Returning to the model of FIG. 6E, the generation of hydrogen ions by extension reactions and the fluxes through microwells with beads and those without may be described by simple reaction-diffusion equations, which give the change in hydrogen ion concentrations at the sensors, as illustrated by the following equations:

$$\frac{s_t - s_b}{\alpha_b} = \phi_b = \frac{\partial s_b}{\partial t}\beta_b \quad \frac{s_t - s_e}{\alpha_e} = \phi_e = \frac{\partial s_e}{\partial t}\beta_e$$

where $\alpha_b$ and $\alpha_e$ are diffusion constants of the hydrogen ions in the solvent, and $\beta_b$ and $\beta_e$ are constants that reflect the interaction (e.g. buffering) of the hydrogen ions with microwell wall and/or particle or analyte in the microwell. Manipulation of these terms and integration of the differentials gives $s_b$ as a function of $s_e$ and an integral of the differences between $s_b$ and $s_e$. To this expression is added a source term, $I_{ext}$, for the hydrogen ions generated in an extension reaction.

$$s_b = s_e R + \frac{\int s_e - s_b}{\tau_b} + I_{ext}$$

where $R=(\alpha_e\beta_e/\alpha_b\beta_b)$. Curves for $s_b$ are readily generated numerically for fitting data to remove reagent change noise. FIG. 6F illustrates data fit by such a model and use of the model to subtract reagent change noise. Panel (650) shows an output signal (652) ("NN Data") from a sensor of a microwell in which extension reactions occur when exposed to flows of dATP and dGTP. Curve (654) ("Model Background") is from the above model of the reagent change noise. Panel (656) shows curve (658) which models both the reagent change noise and the generation of hydrogen ions. Panel (659) shows output signal (657) after the reagent change noise has been subtracted.

In FIG. 6D, each template includes calibration sequence (685) that provides a known signal in response to the introduction of initial dNTPs. Preferably, calibration sequence (685) contains at least one of each kind of nucleotide. In one aspect, calibration sequence (685) is from 4 to 6 nucleotides in length and may contain a homopolymer or may be non-homopolymeric. Calibration sequence information from neighboring microwells may be used to determine which neighboring microwells contain templates capable of being extended which, in turn, allows identification of neighboring microwells that may generate 0-mer signals, 1-mer signals, and so on, in subsequent reaction cycles. Information from such signals from neighboring microwell may be used to subtract undesired noise components from output signals of interest. In other embodiments, an average 0-mer signal may be modeled (referred to herein as a "virtual 0-mer" signal) by taking into account (i) neighboring empty well output signals in a given cycle, and (ii) the effects of the presence of a particle and/or template on the shape of the reagent change noise curve. The latter factor as noted in FIG. 2D is a delay, which is reflected in a flattening and shifting in the positive time direction of an output signal of a particle-containing microwell relative to an output signal of an empty well. As noted, such effects are readily modeled to convert empty well output signals to virtual 0-mer output signals, which may be used to subtract reagent change noise.

Figure 7A:
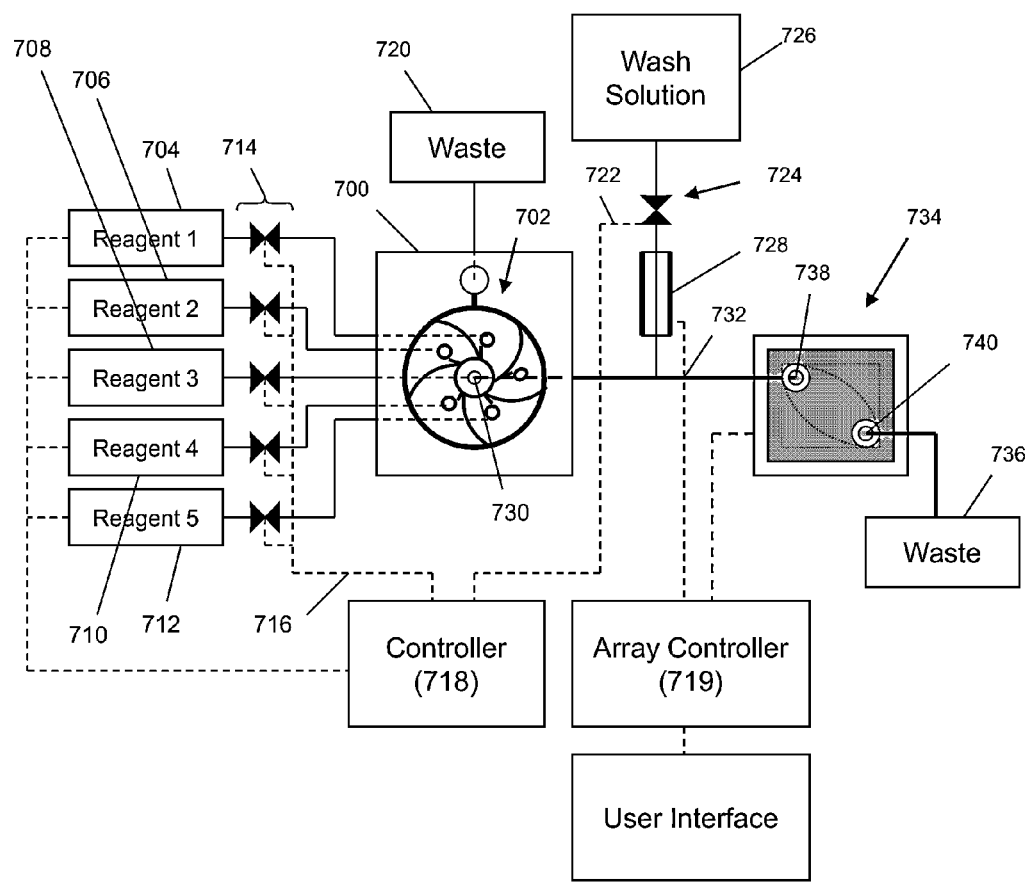
FIGS. 7A-7C are diagrammatic illustrations of components of an apparatus of the invention adapted for pH-based DNA sequencing.
Figure 7B:
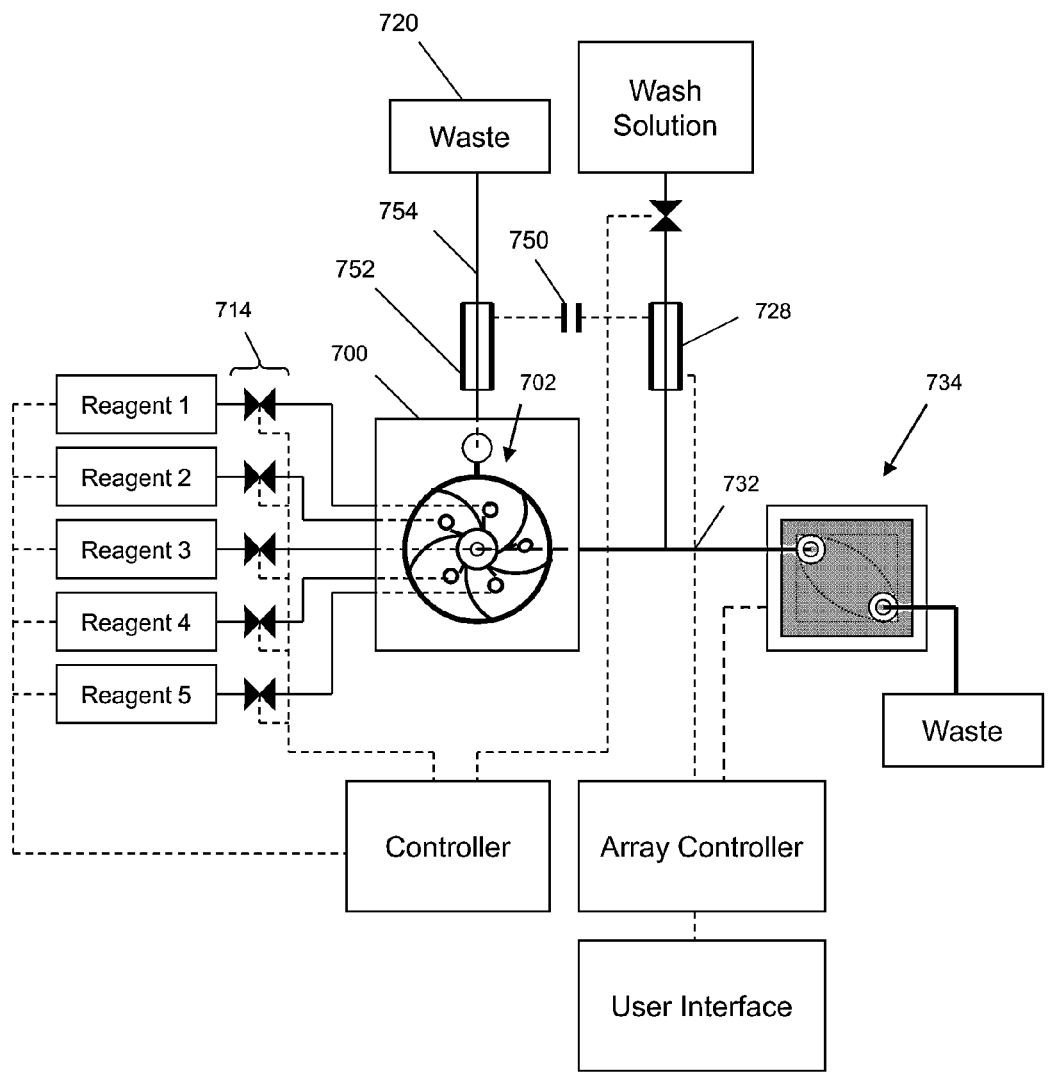
Figure 7C:
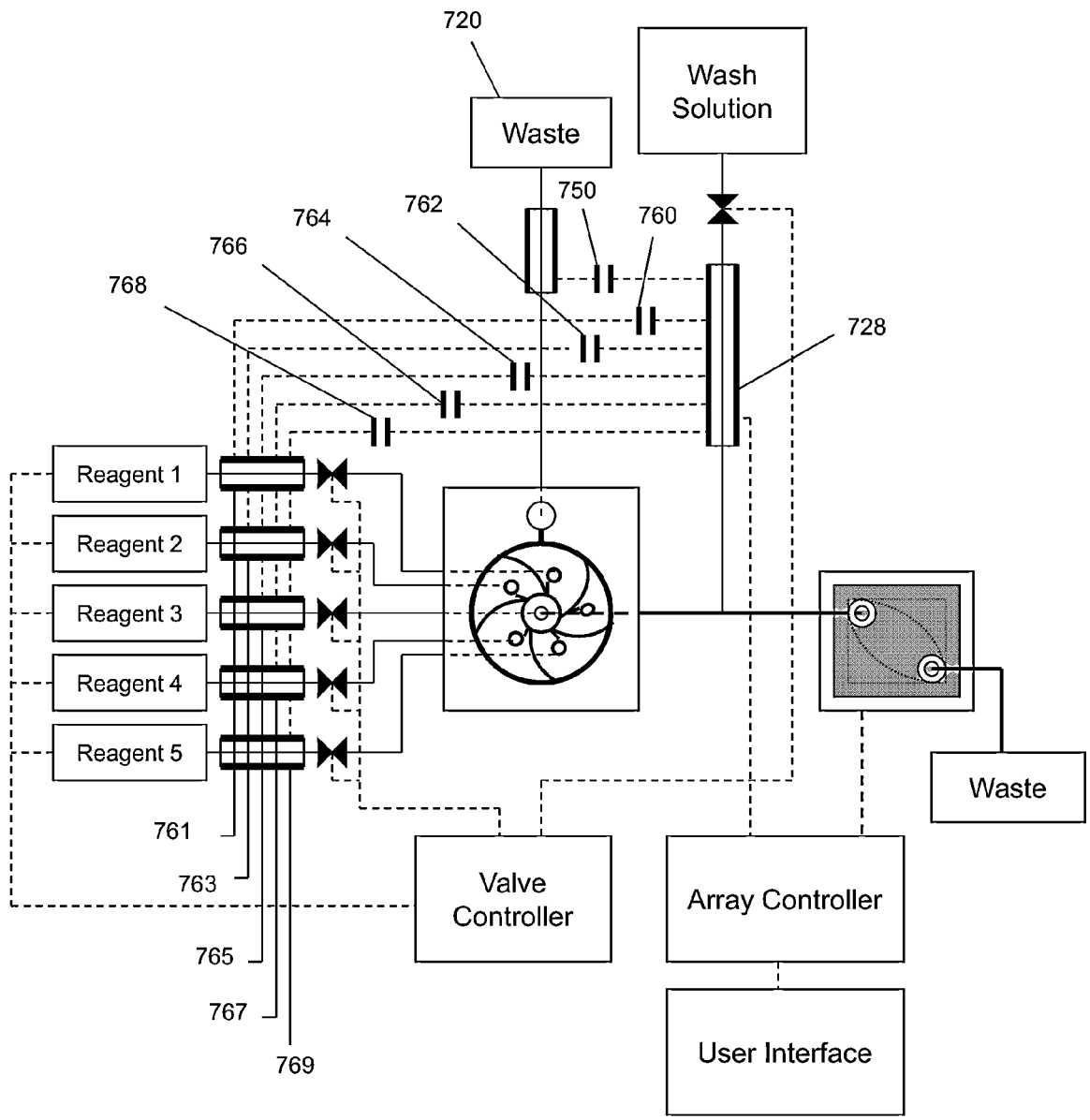

FIG. 7A diagrammatically illustrates an apparatus that may be used to carry out pH-based nucleic acid sequencing in accordance with Rothberg et al, U.S. patent publication 2009/0026082. Housing (700) containing fluidics circuit (702, described more fully below) is connected by inlets to reagent reservoirs (704, 706, 708, 710, and 712), to waste reservoir (720), and to flow cell (734) by passage (732) that connects fluidics node (730) to inlet (738) of flow cell (734). Reagents from reservoirs (704, 706, 708, 710, and 712) may be driven to fluidic circuit (702) by a variety of methods including pressure, pumps, such as syringe pumps, gravity feed, and the like, and are selected by control of valves (714). Controller (718) includes controllers for valves (714) that generate signals for opening and closing via electrical connection (716). Controller (718) also includes controllers for other components of the system, such as wash solution valve (724) connected thereto by (722). Array controller (719) includes control and data acquisition functions for flow cell (734) and reference electrode (728). In one mode of operation, fluidic circuit (702) delivers a sequence of selected reagents (1, 2, 3, 4, or 5) to flow cell (734) under programmed control of controller (718), such that in between selected reagent flows fluidics circuit (702) is primed and washed, and flow cell (734) is washed. Fluids entering flow cell (734) exit through outlet (740) and are deposited in waste container (736). Throughout such an operation, the reactions and/or measurements taking place in flow cell (734) are assured a stable reference voltage because fluidics circuit (702) provides reference electrode (728) with a continuous, i.e. uninterrupted, electrolyte pathway with flow cell (734), although it is in physical contact with only the wash solution.

FIGS. 7B and 7C illustrate further measures that may be taken to reduce noise introduced into other parts of fluidics system that may affect the reference voltage. In FIG. 7B, electrode (752) forming part of waste stream (754) is coupled to reference electrode (728) by capacitor (750), which filters low frequency noise introduced through waste stream (754). Likewise, as shown in FIG. 7C, such electrodes (761, 763, 765, 767, and 769) may be fitted on flow paths for process reagents, such as reagents 1 through 5, and coupled to reference electrode (728) through separate capacitors (760, 762, 764, 766, and 768, respectively).

Fluidics Circuits for Sequential Reagent Delivery

Figure 8A:
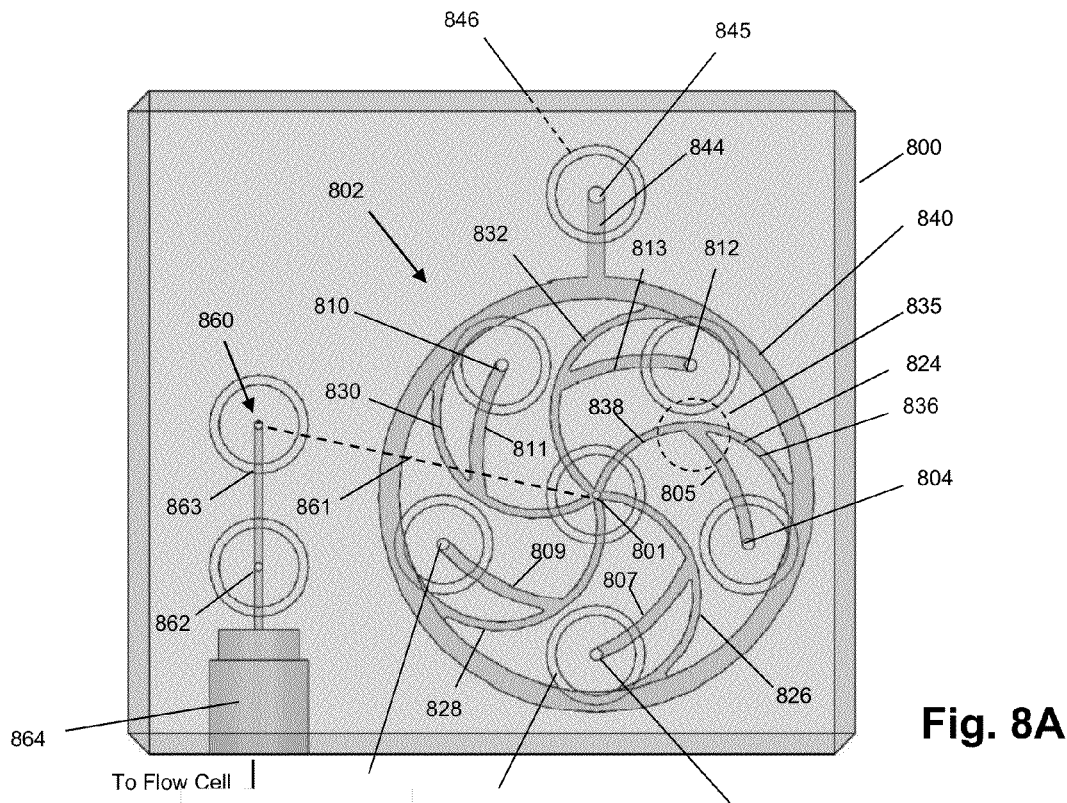
FIGS. 8A-8C diagrammatically illustrate a fluid circuit for delivering successively different reagents to a flow cell for DNA sequencing, where a reference electrode is in continuous fluid contact with solely a wash solution.
Figure 8B:
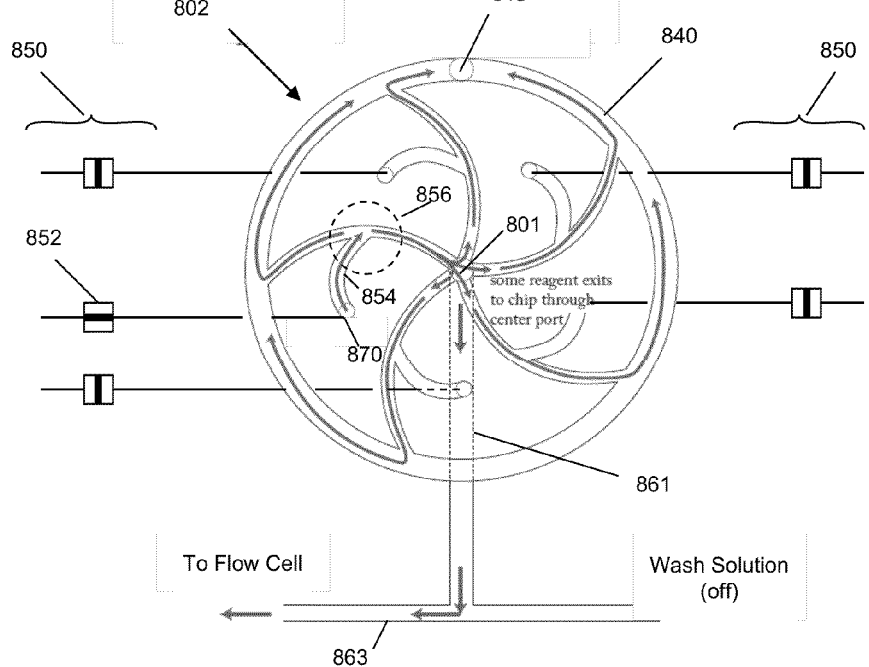
Figure 8C:
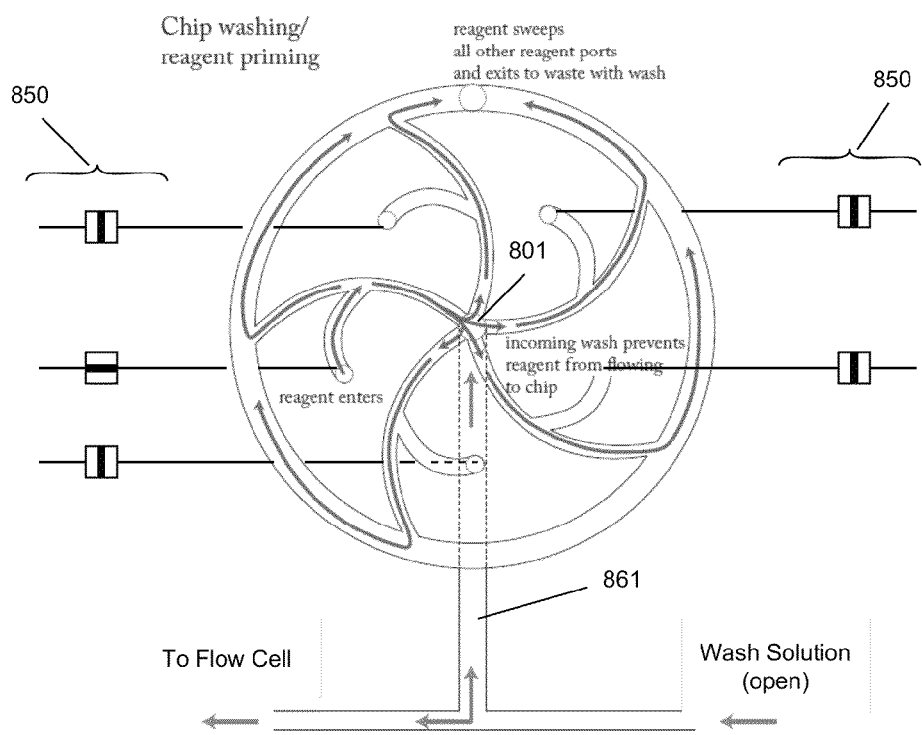

As mentioned above, in one embodiment, a reference electrode of the invention is kept in contact with only a single reagent by use of a fluidic circuit, such as (702) in FIG. 7A. FIGS. 8A-8C diagrammatically illustrate an embodiment of a fluidics circuit which provides this contact for the reference electrode and which accommodates five input reagents in a planar circuit structure. FIG. 8A is a top view of a transparent body or housing (800) containing fluidic circuit (802) which may comprise a microfluidics device. Housing (800) may be constructed from a variety of materials, including metals, glass, ceramics, plastics, or the like. Transparent materials include polycarbonate, polymethyl methacryate, and the like. Inlets (or input ports) (804, 806, 808, 810, and 812) are connected by a passage to their respective connector slots (814) located on the bottom side of housing (800) (shown as double circles concentric with the inlets) from which reagents enter fluidic circuit (802). Inlets (804, 806, 808, 810, and 812) are in fluid communication with passages (805, 807, 809, 811, and 813, respectively) which, in turn, are connected to curvilinear passages (824, 826, 828, 830, and 832, respectively). Each curvilinear passage consists of two legs, such as (836) and (838), identified for curvilinear passage (824) at a "T" junction (835), also identified for only curvilinear passage (824). One leg is an inner leg (for example (838)) which connects its respective inlet to node (or multi-use central port) (801) and the other leg is an outer leg (for example (836)) which connects its respective inlet to waste passage (or ring) (840). As mentioned above, the cross-sectional areas and lengths of the inner and outer legs of the curvilinear passages may be selected to achieve the desired balance of flows at the "T" junctions and at node (801). Through passage (844), waste passage (or channel) (840) is in fluid communication with waste port (845) which connects to a waste reservoir (not shown) by connector slot (846) on the bottom side of body (800). Node (801) is in fluid communication with port (860) by passage (861) which in this embodiment is external to body (800) and is illustrated by a dashed line. In other embodiments, passage (861) may be formed in body (800) so that connector slots for node (801) and port (860) are not required. Port (860) is connected by passage (863) to wash solution inlet (862), where a "T" junction is formed, and to connector slot (864) which, in turn, provides a conduit to a flow cell, reaction chamber, or the like. FIGS. 8B and 8C illustrate two of three modes of using the fluidics circuit to distribute fluids to a flow cell. The modes of operation are implemented by valves (850) associated with each of the input reagents and with the wash solution. In a first mode of operation (selected reagent valve open, all other reagent valves closed, wash solution valve closed) (FIG. 8B), a selected reagent is delivered to a flow cell; in a second mode of operation (selected reagent valve open, all other reagent valves closed, wash solution valve open) (FIG. 8C), the fluidic circuit is primed to deliver a selected reagent; and in a third mode of operation (all reagent valves closed, wash solution valve open) (not shown), all passages in the fluidics circuit are washed. As mentioned above, associated with each inlet is a valve (850) which can be opened to allow fluid to enter fluidic circuit (802) through its respective inlet (as shown for valve (852)), or closed to prevent fluid from entering circuit (802) (as shown with all valves, except for (852)). In each case, when an inlet's valve is open and the others are closed (including the wash solution valve) as shown for inlet (870) in the FIG. 8B, fluid flows through passage (854) to "T" junction (856) where it is split into two flows, one of which is directed to waste passage (840) and then the waste port (845), and another of which is directed to node (801). From node (801) this second flow again splits into multiple flows, one of which exits node (801) through passage (861) and then to passage (863) and to a flow cell, and the other flows to each of the passages connecting node (801) to the other inlets, and then to waste passage (840) and waste port (845). The latter flows pass the other inlets carrying any material diffusing or leaking therefrom and directing it to waste port (845). A sequence of different reagents may be directed to a flow cell by opening the valve of a selected reagent and simultaneously closing the valves of all of the non-selected reagents and the wash solution. In one embodiment, such sequence may be implemented by a sequence of operating modes of the fluidics circuit such as: wash, prime reagent $x_1$, deliver reagent $x_1$, wash, prime reagent $x_2$, deliver reagent $x_2$, wash, and so on. The reagent priming mode of operation is illustrated in FIG. 8C. As in the reagent delivery mode, all reagent inlet valves are closed, except for the valve corresponding to the selected reagent. Unlike the reagent delivery mode, however, the wash solution valve is open and the relative pressure of the selected reagent flow and the wash solution flow is selected so that wash solution flows through passage (861) and into node (801) where it then exits through all the passages leading to waste passage (840), except for the passage leading to the selected reagent inlet.

Definitions

"Amplicon" means the product of a polynucleotide amplification reaction: that is, a clonal population of polynucleotides, which may be single stranded or double stranded, which are replicated from one or more starting sequences. The one or more starting sequences may be one or more copies of the same sequence, or they may be a mixture of different sequences that contain a common region that is amplified, for example, a specific exon sequence present in a mixture of DNA fragments extracted from a sample. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4.965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. As used herein, the term "amplifying" means performing an amplification reaction. A "reaction mixture" means a solution containing all the necessary reactants for performing a reaction, which may include, but be not limited to, buffering agents to maintain pH at a selected level during a reaction, salts, co-factors, scavengers, and the like. A "solid phase amplicon" means a solid phase support, such as a particle or bead, having attached a clonal population of nucleic acid sequences, which may have been produced by a process such as emulsion PCR, or like technique.

"Analyte" means a molecule or biological cell of interest that directly affects an electronic sensor at a sample retaining region, such as a microwell, or that indirectly affects such an electronic sensor by a byproduct from a reaction involving such molecule or biological cell located in such a sample retaining region, or reaction confinement region, such as a microwell. In one aspect, analyte is a nucleic acid template that is subjected to a sequencing reaction which, in turn, generates a reaction byproduct, such as hydrogen ions, that affects an electronic sensor. The term "analyte" also comprehends multiple copies of analytes, such as proteins, peptide, nucleic acids, or the like, attached to solid supports, such as beads or particles. In a one embodiment, the term "analyte" means a nucleic acid amplicon or a solid phase amplicon.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for case of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858, 195; 6,010,607; and 6,033,546; Soane et al, U.S. Pat. Nos. 5,126,022 and 6,054,034; Nelson et al, U.S. Pat. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Microwell," which is used interchangeably with "reaction chamber," means a special case of a "reaction confinement region," that is, a physical or chemical attribute of a solid substrate that permit the localization of a reaction of interest. Reaction confinement regions may be a discrete region of a surface of a substrate that specifically binds an analyte of interest, such as a discrete region with oligonucleotides or antibodies covalently linked to such surface. Usually reaction confinement regions are hollows or wells having well-defined shapes and volumes which are manufactured into a substrate. These latter types of reaction confinement regions are referred to herein as microwells or reaction chambers, and may be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Preferable configurations (e.g. spacing, shape and volumes) of microwells or reaction chambers are disclosed in Rothberg et al, U.S. patent publication 2009/0127589; Rothberg et al, U.K. patent application GB24611127, which are incorporated by reference. Microwells may have square, rectangular, or octagonal cross sections and be arranged as a rectilinear array on a surface. Microwells may also have hexagonal cross sections and be arranged as a hexagonal array, which permit a higher density of microwells per unit area in comparison to rectilinear arrays. Exemplary configurations of microwells are as follows: In some embodiments, the reaction chamber array comprises $10^2$, $10^3$, $10^4$, $10^5$, $10^6$ or $10^7$ reaction chambers. As used herein, an array is a planar arrangement of elements such as sensors or wells. The array may be one or two dimensional. A one dimensional array is an array having one column (or row) of elements in the first dimension and a plurality of columns (or rows) in the second dimension. The number of columns (or rows) in the first and second dimensions may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Briefly, in one embodiment microwell arrays may be fabricated as follows: After the semiconductor structures of a sensor array are formed, the microwell structure is applied to such structure on the semiconductor die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 3-12 µm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter.) Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-methyl-ortho-silicate (TEOS). The invention encompasses an apparatus comprising at least one two-dimensional array of reaction chambers, wherein each reaction chamber is coupled to a chemically-sensitive field effect transistor ("chemFET") and each reaction chamber is no greater than $10\,\mu m^3$ (i.e., 1 µL) in volume. Preferably, each reaction chamber is no greater than 0.34 µL, and more preferably no greater than 0.096 µL or even 0.012 µL in volume. A reaction chamber can optionally be $2^2, 3^2, 4^2, 5^2, 6^2, 7^2, 8^2, 9^2,$ or $10^2$ square microns in cross-sectional area at the top. Preferably, the array has at least $10^2, 10^3, 10^4, 10^5, 10^6, 10^7, 10^8, 10^9$, or more reaction chambers. The reaction chambers may be capacitively coupled to the chemFETs, and preferably are capacitively coupled to the chemFETs.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Diefenbach, editor, PCR Primer: A Laboratory Manual, $2^{nd}$ Edition (Cold Spring Harbor Press, New York, 2003).

What is claimed is:

1. An apparatus for performing multi-step electrochemical reactions, the apparatus comprising:
   one or more reaction vessels each coupled to an electronic sensor for monitoring products in the one or more reaction vessels, the electronic sensor generating an output signal related to a concentration or presence of a product, the output signal depending on a reference voltage;
   a fluidics system for sequentially delivering a plurality of electrolytes to the one or more reaction vessels one at a time, the fluidics system including a plurality of electrolyte reservoirs in fluidic communication through a valve block to a common passage, the common passage in fluidic communication between the valve block and the one or more reaction vessels, a wash solution reservoir in fluidic communication with the common passage via a branch passage connected with the common passage at a junction between the valve block and the one or more reaction vessels; and
   a reference electrode in contact with a wash solution within the branch passage, the reference electrode being in electrical communication with the one or more reaction vessels through fluid extending from the branch passage and through the common passage and providing the reference voltage to each electronic sensor without the reference electrode contacting any of the plurality of electrolytes.

2. The apparatus of claim 1 wherein said one or more reaction vessels is an array of microwells disposed on an array of chemically sensitive field-effect transistor sensors and wherein said fluidics system comprises a flow cell in fluid communication with the microwells and configured to deliver reactant electrolytes to each microwell at substantially the same flow rate.

3. The apparatus of claim 1, wherein said reference electrode is disposed in the branch passage between a valve and the junction such that said reference electrode is in electric communication with said one or more reaction vessels and such that whenever the valve is shut and fluid within the branch passage is stationary and substantially none of the plurality of electrolytes contacts said reference electrode.

4. The apparatus of claim 1 wherein said fluidics system comprises a plurality of electrolyte passages delivering said plurality of electrolytes from the electrolyte reservoirs to said one or more reaction vessels and to at least one waste reservoir, each of the plurality of electrolyte passages being connected to an electrode that is capacitively connected to said reference electrode.

5. An article of manufacture comprising:
   a sensor array comprising a plurality of sensors formed in a circuit-supporting substrate, each sensor of the array being configured to generate at least one electrical signal related to a concentration or presence of one or more predetermined species proximate thereto and a microwell array disposed on the circuit-supporting substrate such that each microwell thereof has an opening on a surface of the microwell array and is disposed on at least one sensor;
   a plurality of analytes randomly distributed in the microwells at locations determinable by an output signal generated by its corresponding sensor;
   a fluidics system for sequentially delivering a plurality of reagents to the microwell array one at a time, the fluidics system including a plurality of reagent reservoirs in fluidic communication through a valve block to a common passage, the common passage in fluidic communication between the microwell array and the valve block, a wash solution reservoir in fluidic communication with the common passage via a branch passage connected with the common passage at a junction between the valve block and the microwell array; and a reference electrode in contact with a wash solution within the branch passage, the reference electrode being in electrical communication with sensors of the plurality of sensors through fluid extending from the branch passage and through the common passage and providing a reference voltage to the sensors of the plurality of sensors without the reference electrode contacting any of the plurality of reagents.

6. The article of claim 5 wherein said location of each of said analytes is determined by a delay in a change of said output signal in response to a change in concentration of said one or more predetermined species at said surface of said microwell array.

7. The article of claim 6 wherein said one or more predetermined species is hydrogen ion and wherein said change in said concentration thereof is a step function having a change in magnitude of pH 1.0 or less.

8. The article of claim 5 wherein said analytes each comprise a particle having attached thereto a clonal population of nucleic acid fragments.

9. The apparatus of claim 1 further comprising a flow cell having an inlet, an outlet and a flow chamber that defines a flow path from the inlet to the outlet, wherein the flow chamber is configured to deliver the wash solution and the plurality of electrolytes transversely over open portions of the one or more reaction vessels in the flow path.

10. The apparatus of claim 1 wherein the electronic sensor includes a chemically sensitive field-effect transistor.

11. The apparatus of claim 1 further comprising a plurality of analytes randomly distributed in the one or more reaction vessels.

12. The apparatus of claim 11 wherein the plurality of analytes comprise a particle having attached thereto a clonal population of nucleic acid fragments.

13. The apparatus of claim 11 wherein the electronic sensor is to generate the output signal in response to an analyte or analyte reaction byproduct proximate thereto.

14. The article of claim 5 further comprising a flow cell having an inlet, an outlet and a flow chamber that defines said flow path from the inlet to the outlet; and the flow chamber being configured so that said plurality of reagents are delivered in a flow parallel to a surface of said sensor array across.

* * * * *

UNITED STATES PATENT AND TRADEMARK OFFICE
CERTIFICATE OF CORRECTION

PATENT NO.         : 8,673,627 B2                              Page 1 of 1
APPLICATION NO.    : 12/785716
DATED              : March 18, 2014
INVENTOR(S)        : Nobile et al.

It is certified that error appears in the above-identified patent and that said Letters Patent is hereby corrected as shown below:

On the Title page Item [57] Line 4 following "sensors" and before "noise conditions" delete "underminimal" and insert --under minimal--.

Signed and Sealed this
Twenty-second Day of July, 2014

Michelle K. Lee
*Deputy Director of the United States Patent and Trademark Office*